(12) United States Patent
Dinkelborg et al.

(10) Patent No.: US 9,375,497 B2
(45) Date of Patent: Jun. 28, 2016

(54) [F-18]-LABELED L-GLUTAMIC ACID, [F-18]-LABELED L-GLUTAMINE, DERIVATIVES THEREOF AND USE THEREOF AND PROCESSES FOR THEIR PREPARATION

(71) Applicant: BAYER SCHERING PHARMA AKTIENGESELLSCHAFT, Berlin (DE)

(72) Inventors: Ludger Dinkelborg, Berlin (DE); Matthias Friebe, Berlin (DE); Nikolaevna Raisa Krasikowa, St. Petersburg (RU); Yuri Belokon, Moscow (RU); Fedorovna Olga Kuznetsova, St. Petersburg (RU); Keith Graham, Berlin (DE); Lutz Lehmann, Wuppertal (DE); Mathias Berndt, Berlin (DE)

(73) Assignee: PIRAMAL IMAGING SA, Matran (CH)

( * ) Notice: Subject to any disclaimer, the term of this patent is extended or adjusted under 35 U.S.C. 154(b) by 0 days.

(21) Appl. No.: 14/153,491

(22) Filed: Jan. 13, 2014

(65) Prior Publication Data
US 2014/0301948 A1    Oct. 9, 2014

Related U.S. Application Data

(63) Continuation of application No. 12/513,112, filed as application No. PCT/EP2007/009518 on Oct. 30, 2007, now abandoned.

(30) Foreign Application Priority Data

Nov. 1, 2006  (RU) .............................. 2006138584
Nov. 18, 2006  (EP) .................................... 06090211

(51) Int. Cl.
| | | |
|---|---|---|
| *A61K 51/00* | (2006.01) | |
| *A61M 36/14* | (2006.01) | |
| *A61K 51/04* | (2006.01) | |
| *C07B 59/00* | (2006.01) | |
| *C07C 229/24* | (2006.01) | |
| *C07C 251/24* | (2006.01) | |
| *C07C 271/22* | (2006.01) | |
| *C07C 309/66* | (2006.01) | |
| *C07C 309/73* | (2006.01) | |
| *C07D 207/16* | (2006.01) | |
| *C07D 207/28* | (2006.01) | |
| *C07C 227/16* | (2006.01) | |
| *C07D 207/26* | (2006.01) | |
| *C07F 15/04* | (2006.01) | |

(52) U.S. Cl.
CPC ........... *A61K 51/0402* (2013.01); *C07B 59/001* (2013.01); *C07C 227/16* (2013.01); *C07C 229/24* (2013.01); *C07C 251/24* (2013.01); *C07C 271/22* (2013.01); *C07C 309/66* (2013.01); *C07C 309/73* (2013.01); *C07D 207/16* (2013.01); *C07D 207/26* (2013.01); *C07D 207/28* (2013.01); *C07F 15/045* (2013.01); *C07B 2200/05* (2013.01)

(58) Field of Classification Search
CPC ............. A61K 51/0402; C07B 59/001; C07B 2200/05; C07C 229/24; C07C 251/24; C07C 271/22; C07C 309/66; C07C 309/73; C07C 227/16; C07D 207/16; C07D 207/26; C07D 207/28; C07F 15/045
USPC ........................................................ 424/1.89
See application file for complete search history.

(56) References Cited

U.S. PATENT DOCUMENTS

| | | | |
|---|---|---|---|
| 3,444,187 A | 5/1969 | Jisaburo et al. | |
| 5,264,570 A | 11/1993 | Johnson et al. | |
| 5,589,501 A | 12/1996 | Carrera et al. | |
| 5,739,164 A | 4/1998 | Carrera et al. | |
| 7,189,383 B2 | 3/2007 | Mertens | |
| 7,483,732 B2 | 1/2009 | Zhong et al. | |
| 2002/0115688 A1 | 8/2002 | Beart et al. | |
| 2005/0004082 A1* | 1/2005 | Dasseux et al. | ............... 514/106 |
| 2005/0240098 A1 | 10/2005 | Zhong et al. | |
| 2006/0127306 A1 | 6/2006 | Mertens | |
| 2007/0081941 A1 | 4/2007 | Mertens | |
| 2010/0217011 A1 | 8/2010 | Dinkelborg et al. | |
| 2010/0290991 A1 | 11/2010 | Friebe et al. | |
| 2011/0064673 A1 | 3/2011 | Dinkelborg et al. | |
| 2011/0165076 A1 | 7/2011 | Dinkelborg et al. | |

FOREIGN PATENT DOCUMENTS

| | | |
|---|---|---|
| CA | 2667395 | 5/2008 |
| EP | 1923382 | 11/2006 |
| FR | 1461184 | 1/1966 |
| FR | 14611184 A | 1/1966 |

(Continued)

OTHER PUBLICATIONS

Barnett et al. CRC Crit. Rev. Biochem. 1984, 15, 201-235.*
Patel et al. Neuropharmacol. 2004, 46, 273-284.*
Baker, S. R. et al., "Radical reactions leading to substituted pyroglutamates," Tetrahedron Letters, Apr. 30, 1998, vol. 39, No. 18, pp. 2815-2818.
Baldwin, J. E. et al., "Synthesis of nonproteinogenic amino acids part 2: Preparation of a synthetic equivalent of the gamma anion synthon for asymmetric amino acid synthesis," Tetrahedron, 1989, vol. 45, No. 5, pp. 1453-1464.
Belokon, Y. N. et al., "Synthesis of enantio- and diastero-isomerically pure .beta.- and .gamma.-substituted glutamic acids via glycine condensation with activated olefins," Database CA [Online], Chemical Abstracts Service, Journal of the Chemical Society, Perkin Transactions 1: Organic and Bio-organic Chemistry, 1986, No. 11, pp. 1865-1872.

(Continued)

*Primary Examiner* — Michael G Hartley
*Assistant Examiner* — Sean R Donohue
(74) *Attorney, Agent, or Firm* — Millen, White, Zelano & Branigan, P.C.

(57) ABSTRACT

The compounds and the synthesis of [F-18]-labeled L-glutamic acid, [F-18]-labeled L-glutamate, their derivatives as set forth in formula (I) and their uses are described.

8 Claims, 6 Drawing Sheets

(56) References Cited

FOREIGN PATENT DOCUMENTS

| JP | 8020564 | 1/1996 |
|----|---------|--------|
| JP | 2006516547 | 7/2006 |
| JP | 2007532259 | 11/2007 |
| JP | 2010508317 | 3/2010 |
| WO | WO0214261 | 2/2002 |
| WO | WO0218941 | 3/2002 |
| WO | WO03099746 | 12/2003 |
| WO | WO 03099746 A1 * | 12/2003 |
| WO | WO2004110500 | 12/2004 |
| WO | WO2005101045 | 10/2005 |
| WO | WO2008052788 | 5/2008 |

OTHER PUBLICATIONS

Chinese Official Action related to corresponding Chines Patent Application No. 200980118540.7 dated Oct. 29, 2013.
De Dios, A. et al., "4-Substituted d-Glutamic Acid Analogues: The First Potent Inhibitors of Glutamate Racemase (MurI) Enzyme with Antibacterial Activity," J. Med. Chem., 2002, vol. 45, pp. 4559-4570.
English Translation of Office Action issued Dec. 10, 2013 in related Japanese Patent Application No. 2011-509884.
English Translation of Office Action issued Dec. 10, 2013 in related Japanese Patent Application No. 2011-509883.
Escribano, A. et al., "(2S,4S)-2-Amino-4-(2,2-Diphenylethyl)Pentanedioic Acid Selective Group 2 Metabotropic Glutamate Receptor Antagonist," Bioorganic & Medicinal Chemistry Letters 8, 1998, pp. 765-770.
International Search Report for PCT/EP2007/009518 dated Jan. 28, 2008.
International Search Report for PCT/EP2009/003419 dated Aug. 24, 2009.
International Search Report for PCT/EP2009/003420 dated Aug. 26, 2009.
Jeong, M. J. et al., "Synthesis of no-carrier-added [18F]Fluoroacetate," Journal of Labelled Compounds and Radiopharmaceuticals, 1997, vol. 39, No. 5, pp. 395-399.
Laverman, P. et al., "Fluorinated amino acids for tumor imaging with positron emission tomography," European Journal of Nuclear Medicine, 2002, vol. 29, No. 5, pp. 681-690.
Office Action issued Dec. 10, 2013 in related Japanese Patent Application No. 2011-509884.
Office Action issued Dec. 10, 2013 in related Japanese Patent Application No. 2011-509883.
Office Action issued Nov. 15, 2013 in related Canadian Patent Application No. 2667395.
Pohlman, M. et al., "Efficient Stereoselective syntheses of cyclic amino acids via Michael-Induced Ring-Closing Reactions," Database CAPLUS [Online], Chemical Abstracts Service, Organic Letters, 2003, vol. 5, No. 15, pp. 2631-2633.
Powell, A. et al., "Precursor-directed biosynthesis of nonribosomal lipopeptides with modified glutamate residues," Chem. Commun., 2007, pp. 2683-2685.
Shiue, C. Y. et al., "Synthesis of no-carrier-added (NCA) [18F]fluoroalkyl halides and their application in the synthesis of [18F]Fluoroalkyl derivatives of neurotransmitter receptor active compounds," Journal of Labelled Compounds and Radiopharmaceuticals, 1987, vol. 24, No. 1, pp. 55-64.
Souba, W. W. et al., "Glutamine and Cancer," Annals of Surgery, 1993, vol. 218, No. 6, pp. 715-728.
Wakamiya, T. et al., "Synthesis and stereochemistry of carnosadine, a new cyclopropyl amino acid from red alga grateloupia carnosa," Tetrahedron Letters, 1986, vol. 27, No. 19, pp. 2143-2144.
Unkeless, J. C. et al., "The diastereomers of $\gamma$-Fluoroglutamate: Complementary Structural Analogues," Molecular Pharmacology, May 1971, vol. 7, pp. 293-300.
Viscontini, M. et al., "Pyrrolizidine chemistry. VII. Preparation of I-proline and trans-3-hydroxy-dl-proline by electrochemical reduction of the corresponding pyrrolidone-2-carboxylic acids," Database CAPLUS [Online], Chemical Abstracts Service, Helvetica Chemica Acta, 1966, vol. 49, No. 8, pp. 2524-2526.
Wu, F. et al., "Uptake of 14c- and 11c-labeled glutamate, glutamine and asparate in vitro and in vivo," Anticancer Research, Jan. 2000, vol. 20, No. 1A, pp. 251-256.
English Abstract of JP-8020564, Publication Date: Jan. 23, 1995.
English Abstract of WO03099746, Publication Date: Dec. 4, 2003.
English Abstract of EP-1923382, Publication Date: May 21, 2008.
Office Action for related Chinese Patent Application No. 200780040971.7 dated Mar. 20, 2014.
English Translation of Office Action for related Chinese Patent Application No. 200780040971.7 dated Mar. 20, 2014.
Office Action for related Korean Patent Application No. 10-2009-70009017 dated Apr. 23, 2014.
English Translation of Office Action for related Korean Patent Application No. 10-2009-70009017 dated Apr. 23, 2014.
Peter Laverman et al., "FLuorinated amino acids for tumour imaging with positron emission tomography", European Journal of Nuclear Medicine, vol. 29, No. 5, May 2002.
Feng Wu, et al. "Uptake of 14C-and 11C-Labeled Glutamate, Glutamine and Aspartate in Vitro and in Vivo", Anticancer Research, 20: pp. 251-256, 2000.
S. Richard Baker, et al., "Radical Reactions Leading to Substituted Pyroglutamates", Tetrahedron Letters 39 (1998), pp. 2815-2818.

* cited by examiner

[F-18]-LABELED L-GLUTAMIC ACID, [F-18]-LABELED L-GLUTAMINE, DERIVATIVES THEREOF AND USE THEREOF AND PROCESSES FOR THEIR PREPARATION

The invention relates to the subjects characterized in the patent claims, namely [F-18]-labeled L-glutamic acid and [F-18]-labeled L-glutamine of the general formula I, their derivatives, and their use and processes for their preparation.

The early diagnosis of malignant tumors plays a very important role in the survival prognosis of a tumor patient. In this diagnosis, noninvasive, diagnostic imaging processes are an important tool. In recent years, PET technology (Positron Emission Tomography), especially, has proven particularly useful. The sensitivity and specificity of PET technology depends significantly on the signal-transmitting substance (tracer) used and its distribution in the body. In the search for suitable tracers, it has been attempted to utilize certain properties of tumors which differentiate tumor tissue from healthy, surrounding tissue. The preferred commercially utilized isotope which is used for PET is $^{18}$F. Owing to its short half life of under 2 hours, $^{18}$F makes particular demands on the preparation of suitable tracers. Laborious, long synthesis routes and purifications are not possible with this isotope, since otherwise a considerable part of the radioactivity of the isotope has already decayed before the tracer can be employed for diagnosis. It is therefore often not possible to use established synthesis routes for nonradioactive fluorinations in the synthesis of $^{18}$F tracers. In addition, the high specific activity of $^{18}$F (about 80 GBq/nmol) leads to very small amounts of [$^{18}$F] fluoride substance for the tracer synthesis, which in turn requires an extreme excess of precursor and makes the success of a radiosynthesis strategy based on nonradioactive fluorination reactions unpredictable.

FDG ([$^{18}$F]2-fluorodeoxyglucose)-PET is a widely accepted and widespread tool in the diagnosis and further clinical monitoring of tumors. Malignant tumors compete with the host organism for the glucose supply to the nutrient supply (Warburg O. Über den Stoffwechsel der Carcinomzelle [Concerning the Metabolism of the Carcinoma Cell]. *Biochem. Zeitschrift* 1924; 152: 309-339; Kellof G. Progress and Promise of FDG-PET Imaging for Cancer Patient Management and Oncologic Drug Development. *Clin Cancer Res.* 2005; 11(8): 2785-2807). Here, tumor cells usually have an increased glucose metabolism in comparison to surrounding cells of the normal tissue. This is utilized in the use of fluorodeoxyglucose (FDG), a glucose derivative, which is transported into the cells in increased amount, but is metabolically trapped there after phosphorylation as FDG 6-phosphate ("Warburg effect"). $^{18}$F-labeled FDG is therefore an effective tracer for the detection of tumors in patients by means of PET technology. In the search for novel PET tracers, recently amino acids have also increasingly been employed for $^{18}$F PET imaging (e.g. (review): *Eur J Nucl Med Mol Imaging.* 2002 May; 29(5):681-90). Here, some of the $^{18}$F-labeled amino acids are suitable for the measurement of the rate of protein synthesis, but most other derivatives for the measurement of direct cell uptake in the tumor. Known $^{18}$F-labeled amino acids are derived, for example, from tyrosine, phenylalanine, proline, asparagine and unnatural amino acids (e.g. *J. Nucl Med* 1991; 32:1338-1346, *J Nucl Med* 1996; 37:320-325, *J Nucl Med* 2001; 42:752-754 and *J Nucl Med* 1999; 40:331-338). Glutamic acid and glutamine are not known as $^{18}$F-labeled derivatives, whereas nonradioactive fluorinated glutamine and glutamic acid derivatives are commonly used; as, for example, those which contain fluorine in the γ-position (for example (review): *Amino Acids.* (2003) April; 24(3):245-61) or in the β-position (for example *Tetrahedron Lett.;* 30; 14; 1989; 1799-1802, *J. Org. Chem.;* 54; 2; 1989; 498-500, Tetrahedron: Asymmetry; 12; 9; 2001; 1303-1312).

It has already been reported in the past on glutamic acid derivatives which have protective groups on the chemical functionalities and a leaving group in the β- or γ-position. Thus information was provided about glutamate as a mesylate or bromide in the γ-position, the acid and amine functions of which were provided with ester or Z protective groups (*J. Chem. Soc. Perkin Trans.* 1; 1986; 1323-1328) or, for example, on γ-chloroglutamic acid without protective groups (*Synthesis;* (1973); 44-46). An account has likewise been given on various occasions of similar derivatives in which, however, the leaving group is positioned in the β-position: for example *Chem. Pharm. Bull.;* 17; 5; (1969); 879-885, *J. Gen. Chem. USSR* (Engl. Transl.); 38; (1968); 1645-1648; *Tetrahedron Lett.;* 27; 19; (1986); 2143-2144, *Chem. Pharm. Bull.; EN;* 17; 5; 1969; 873-878, FR patent 1461184, JP patent 13142.

The present PET tracers which are employed for tumor diagnosis have some indisputable disadvantages: thus although FDG preferably accumulates in those cells having increased glucose metabolism, there is also an increased glucose metabolism in the cells and tissues involved in other pathological and physiological states, for example foci of infection or wound healing (summarized in *J. Nucl. Med. Technol.* (2005), 33, 145-155). It is often still difficult to decide whether a lesion detected by means of FDG-PET is actually of neoplastic origin or is to be attributed to other physiological or pathological states of the tissue. All in all, diagnostic activity by means of FDG-PET in oncology has a sensitivity of 84% and a specificity of 88% (Gambhir et al. "A tabulated summary of the FDG PET literature" *J. Nucl. Med.* 2001, 42, 1-93S). Tumors in the brain can only be very poorly demonstrated, for example, owing to the high accumulation of FDG in healthy brain tissue.

The $^{18}$F-labeled amino acid derivatives known hitherto are in some cases highly suitable for detecting tumors in the brain ((review): *Eur J Nucl Med Mol Imaging.* 2002 May; 29(5): 681-90), however in other tumors they cannot compete with the imaging properties of the "gold standard" [$^{18}$F]2-FDG. The metabolic accumulation and retention of the so far F-18-labeled amino acids in tumorous tissue is generally lower than for FDG. Moreover, the accessibility of isomerically pure F-18-labeled nonaromatic amino acids is chemically very highly demanding.

In a similar manner to glucose, an increased metabolism in proliferating tumor cells has also been described for glutamic acid and glutamine (Medina, *J Nutr.* 1131:2539S-2542S, 2001; Souba, Ann Surg 218: 715-728, 1993). The increased rate of protein and nucleic acid syntheses and the energy generation per se are assumed as reasons for an increased glutamine consumption of tumor cells. The synthesis of corresponding C-11- and C-14-labeled compounds, that are identical with the natural substrate, has already been described in the literature (for example Antoni, Enzyme Catalyzed Synthesis of L-[4-C-11]Aspartate and L-[5-C-11] Glutamate. *J. Labelled Compd. Radiopharm.* 44; (4) 2001: 287-294) and Buchanan, The biosynthesis of showdomycin: studies with stable isotopes and the determination of principal precursors. *J. Chem. Soc. Chem. Commun.; EN;* 22; 1984; 1515-1517). First indications with the C-11-labeled compound do not point to any significant tumor accumulation.

The object of the present invention is to find novel compounds which are suitable in [$^{18}$F]-labeled form for PET-based diagnosis.

The object is achieved by the provision according to the invention of [$^{18}$F]-labeled L-glutamic acid and [$^{18}$F]-labeled L-glutamine, and their derivatives according to the general formula (I), including their diastereomers and enantiomers:

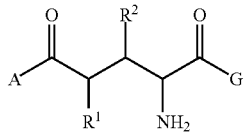
(I)

wherein
A represents
  a) hydroxyl,
  b) branched or unbranched $C_1$-$C_5$ alkoxy,
  c) branched or unbranched hydroxy $C_1$-$C_5$ alkoxy,
  d) branched or unbranched O—$C_1$-$C_5$ alkyl-(O—$C_1$-$C_4$ alkyl)$_n$-O—$C_1$-$C_4$ alkyl,
  e) N($C_1$-$C_5$ alkyl)$_2$,
  f) NH$_2$,
  g) N(H)-L,
  h) O-L, or
  i) O—Z,
G represents
  a) hydroxyl,
  b) branched or unbranched O—$C_1$-$C_5$ alkyl,
  c) branched or unbranched O—$C_2$-$C_5$ alkenyl,
  d) branched or unbranched O—$C_1$-$C_5$ alkyl-(O—$C_1$-$C_4$ alkyl)$_n$-O—$C_1$-$C_4$ alkyl or
  e) branched or unbranched O—$C_2$-$C_5$ alkynyl,
$R^1$ and $R^2$ represent
  a) hydrogen,
  b) $^{18}$F,
  c) branched or unbranched $^{18}$F—$C_1$-$C_5$ alkoxy,
  d) branched or unbranched $^{18}$F—$C_1$-$C_5$ alkyl,
  e) branched or unbranched $^{18}$F-hydroxy-$C_1$-$C_5$ alkyl,
  f) branched or unbranched $^{18}$F—$C_2$-$C_5$ alkenyl, or
  g) branched or unbranched $^{18}$F—$C_2$-$C_5$ alkynyl,
  h) hydroxyl,
  i) branched or unbranched $C_1$-$C_5$ alkyl or
  j) branched or unbranched $C_1$-$C_5$ alkoxy,
with the proviso that exactly one of the substituents $R^1$ or $R^2$ contains exactly one $^{18}$F isotope and the other substituent in each case contains no $^{18}$F isotope,
L represents
  a) branched or unbranched $C_1$-$C_5$ alkyl,
  b) branched or unbranched $C_2$-$C_5$ alkenyl,
  c) branched or unbranched $C_1$-$C_5$ alkyl-(O—$C_1$-$C_4$ alkyl)$_n$-O—$C_1$-$C_4$ alkyl or
  d) branched or unbranched $C_2$-$C_5$ alkynyl,
and
Z represents a metal cation equivalent, which can be mono- or divalent, where divalent metals can lead to ionic bonding with two radicals of the structures according to the invention,
where n is =0, 1, 2 or 3, and where all possible diastereomers and enantiomers are part of the present subject of the invention.

Preferred compounds of the invention according to the formula (I) are distinguished in that
A represents
  a) hydroxyl,
  b) methoxy,
  c) ethoxy,
  d) propoxy,
  e) NMe$_2$,
  f) NEt$_2$,
  g) NH$_2$,
  h) N(H)-L or
  i) O-L,
  j) O—Z.
Further preferred compounds of the invention according to the formula (I) are distinguished in that
A represents
  a) hydroxyl,
  b) methoxy,
  c) ethoxy,
  d) NMe$_2$,
  e) NH$_2$, or
  f) N(H)-L.
Particularly preferred compounds of the invention according to the formula (I) are distinguished in that
A represents
  a) hydroxyl,
  b) methoxy or
  c) NH$_2$.
Preferred compounds of the invention according to the formula (I) are distinguished in that
A represents
  OH.
Preferred compounds of the invention according to the formula (I) are distinguished in that
A represents
  NH$_2$.
Preferred compounds of the invention according to the formula (I) are distinguished in that
G represents
  a) hydroxyl,
  b) methoxy,
  c) ethoxy,
  d) propoxy,
  e) isopropoxy, or
  f) O—$C_2H_4$—OMe.
Further preferred compounds of the invention according to the formula (I) are distinguished in that
G represents
  a) hydroxyl,
  b) methoxy, or
  c) ethoxy.
Particularly preferred compounds of the invention according to the formula (I) are distinguished in that
G represents
  a) hydroxyl or
  b) methoxy.
Preferred compounds of the invention according to the formula (I) are distinguished in that
$R^1$ and $R^2$ represent
  a) hydrogen,
  b) $^{18}$F,
  c) $^{18}$F-methoxy,
  d) $^{18}$F-ethoxy,
  e) $^{18}$F-propoxy,
  f) $^{18}$F-methyl,
  g) $^{18}$F-ethyl, or
  h) $^{18}$F-propyl, with the proviso that exactly one of the substituents $R^1$ or $R^2$ contains exactly one $^{18}F$ isotope and the other substituent in each case is hydrogen.

Further preferred compounds of the invention according to the formula (I) are distinguished in that
$R^1$ and $R^2$ represent
a) hydrogen,
b) $^{18}F$,
c) $^{18}F$-methoxy,
d) $^{18}F$-methyl, or
e) $^{18}F$-ethyl,
with the proviso that exactly one of the substituents $R^1$ or $R^2$ contains exactly one $^{18}F$ isotope and the other substituent in each case is hydrogen.

Particularly preferred compounds of the invention according to the formula (I) are distinguished in that
$R^1$ and $R^2$ represent
a) hydrogen,
b) $^{18}F$ or
c) $^{18}F$-methyl,
with the proviso that exactly one of the substituents $R^1$ or $R^2$ contains exactly one $^{18}F$ isotope and the other substituent in each case is hydrogen.

Particularly preferred compounds of the invention according to the formula (I) are distinguished in that $R^1$ is selected from the group consisting of OH, $CH_3$, $C_2H_5$ and $C_3H_7$, and $R^2$ represents $^{18}F$.

Particularly preferred compounds of the invention according to the formula (I) are distinguished in that $R^2$ is selected from the group consisting of OH, $CH_3$, $C_2H_5$ and $C_3H_7$, and $R^1$ represents $^{18}F$.

Particularly preferred compounds of the invention according to the formula (I) are distinguished in that $R^1$ represents H and $R^2$ represents $^{18}F$.

Particularly preferred compounds of the invention according to the formula (I) are distinguished in that $R^1$ represents $^{18}F$ and $R^2$ represents H.

Preferred compounds of the invention according to the formula (I) are distinguished in that
L represents
a) methyl,
b) ethyl,
c) propyl,
d) isopropyl,
e) —$C_2H_4$—OMe, or
f) —$C_2H_4$—O—$C_2H_4$—OMe.

Particularly preferred compounds of the invention according to the formula (I) are distinguished in that
L represents
a) methyl or
b) ethyl.

Likewise preferred compounds of the invention according to the formula (I) are distinguished in that
Z represents alkali metal and alkaline earth metal ions and also nickel which can be mono- or divalent, where divalent metals can lead to ionic bonding with two radicals of the structures according to the invention.
A preferred Z is selected from the group consisting of $Na^+$, $K^+$, $Ca^{2+}$ and $Mg^{2+}$.

All possible diastereomers and enantiomers of the preferred compounds as set forth in formula (I) are part of the present subject of the invention.

Furthermore particularly preferred is any individual compound of the compounds from the following group, where all possible diastereomers and enantiomers are part of the present subject of the invention:

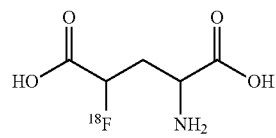
A

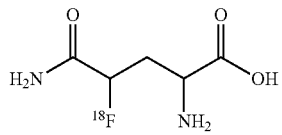
B

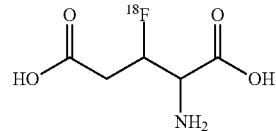
C

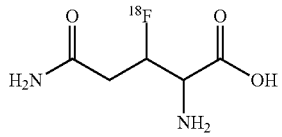
D

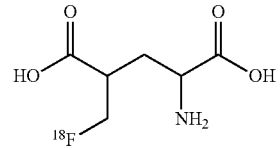
E

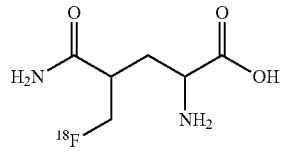
F

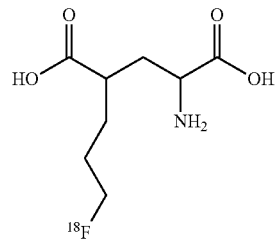
G

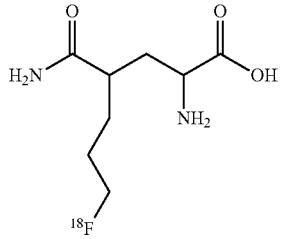
H

-continued

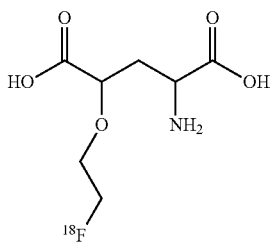

I

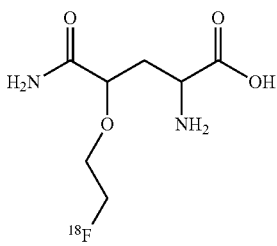

J

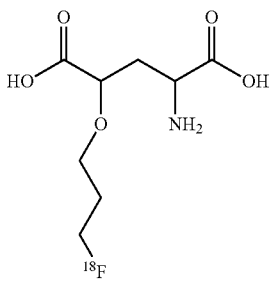

K

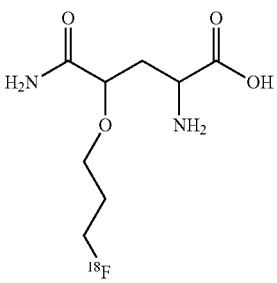

L

The process for the preparation of the compounds of the general formula (I) according to the invention is distinguished in that the compound as set forth in formula (I) is released from a precursor compound of the compound as set forth in formula (II) after introduction of the $^{18}$F isotope. In a second aspect, the present invention thus relates to compounds of the formula (II):

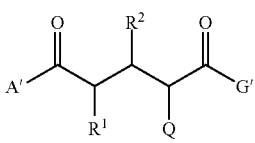

(II)

wherein A' represents
a) hydroxyl,
b) branched or unbranched $C_1$-$C_5$ alkoxy,
c) branched or unbranched hydroxy $C_1$-$C_5$ alkoxy,
d) branched or unbranched O—$C_1$-$C_5$ alkyl-(O—$C_1$-$C_4$ alkyl)$_n$-O—$C_1$-$C_4$ alkyl,
e) N($C_1$-$C_5$ alkyl)$_2$,
f) $NH_2$,
g) N(H)—U,
h) N(H)-L', or
i) O-L', G' represents
a) hydroxyl,
b) O—Z',
c) branched or unbranched O—$C_1$-$C_5$ alkyl,
d) branched or unbranched O—$C_2$-$C_5$ alkenyl,
e) branched or unbranched O—$C_1$-$C_5$ alkyl-(O—$C_1$-$C_4$ alkyl)$_n$-O—$C_1$-$C_4$ alkyl, or
f) branched or unbranched O—$C_2$-$C_5$ alkynyl, $R^1$ and $R^2$ represent
a) hydrogen,
b) $^{18}$F,
c) branched or unbranched $^{18}$F—$C_1$-$C_5$ alkoxy,
d) branched or unbranched $^{18}$F—$C_1$-$C_5$ alkyl,
e) branched or unbranched $^{18}$F-hydroxy-$C_1$-$C_5$ alkyl,
f) branched or unbranched $^{18}$F—$C_2$-$C_5$ alkenyl, or
g) branched or unbranched $^{18}$F—$C_2$-$C_5$ alkynyl,
h) hydroxyl,
i) branched or unbranched $C_1$-$C_5$ alkyl, or
j) branched or unbranched $C_1$-$C_5$ alkoxy,
with the proviso that exactly one of the substituents $R^1$ or $R^2$ contains exactly one $^{18}$F isotope and the other substituent in each case contains no $^{18}$F isotope, Q represents
a) N(H)-tert-butoxycarbonyl,
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
e) N(H)-2,2,2-trichloroethoxycarbonyl,
f) N(H)-1,1-dimethylpropynyl,
g) N(H)-1-methyl-1-phenylethoxycarbonyl,
h) N(H)-1-methyl-1-(4-biphenylyl)ethoxycarbonyl,
i) N(H)-cyclobutylcarbonyl,
j) N(H)-1-methylcyclobutylcarbonyl,
k) N(H)-vinylcarbonyl,
l) N(H)-allylcarbonyl,
m) N(H)-adamantylcarbonyl,
n) N(H)-diphenylmethylcarbonyl,
o) N(H)-cinnamylcarbonyl,
p) N(H)-formyl,
q) N(H)-benzoyl,
r) N(H)-trityl,
s) N(H)-p-methoxyphenyldiphenylmethyl,
t) N(H)-di(p-methoxyphenyl)phenylmethyl,
u)

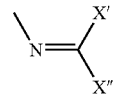

or
v) N-(tert-butoxycarbonyl)$_2$,

L' represents
a) branched or unbranched $C_1$-$C_5$ alkyl,
b) branched or unbranched $C_2$-$C_5$ alkenyl,
c) branched or unbranched $C_1$-$C_5$ alkyl-(O—$C_1$-$C_4$alkyl)$_n$-O—$C_1$-$C_4$alkyl, or
d) branched or unbranched $C_2$-$C_5$ alkynyl, U represents
  a) tert-butoxycarbonyl,
  b) allyloxycarbonyl,
  c) benzyloxycarbonyl,
  d) methoxycarbonyl,
  e) propoxycarbonyl, or
  f) ethoxycarbonyl,
X' and X" independently of one another represent
  a) branched or unbranched $C_1$-$C_5$ alkyl,
  b) substituted or unsubstituted aryl,
  c) aralkyl or
  d) heteroaryl,
and
Z' represents a metal cation equivalent, which can be mono- or divalent, where divalent metals can lead to ionic bonding with two radicals of the structures according to the invention or can form coordinative bonds with a carboxyl and amine function of the amino acid derivative,
A preferred Z' is selected from the group consisting of $Na^+$, $K^+$, $Ca^{2+}$ and $Mg^{2+}$ or
is $Ni^{2+}$,
where n is =0, 1, 2 or 3 and all possible diastereomers and enantiomers are part of the present subject of the invention.

Preferred compounds of the invention according to the formula (II) are distinguished in that
A' represents
  a) hydroxyl,
  b) methoxy,
  c) ethoxy,
  d) tert-butoxy,
  e) $NMe_2$,
  f) $NEt_2$,
  g) $NH_2$,
  h) N(H)—U,
  i) N(H)-L' or
  j) O-L'.

Further preferred compounds of the invention according to the formula (II) are distinguished in that
A' represents
  a) hydroxyl,
  b) methoxy,
  c) ethoxy,
  d) $NMe_2$,
  e) N(H)—U,
  f) $NH_2$, or
  g) N(H)-L'.

Particularly preferred compounds of the invention according to the formula (II) are distinguished in that
A' represents
  a) hydroxyl,
  b) ethoxy,
  b) methoxy,
  c) N(H)—U or
  d) $NH_2$.

Particularly preferred compounds of the invention according to the formula (II) are distinguished in that
A' represents
  a) hydroxyl,
  b) branched or unbranched $C_1$-$C_5$ alkoxy,
  c) —NH-tert-butoxycarbonyl, or
  d) $NH_2$.

Particularly preferred compounds of the invention according to the formula (II) are distinguished in that
A' represents ethoxy.

Particularly preferred compounds of the invention according to the formula (II) are distinguished in that
A' represents $NH_2$.

Preferred compounds of the invention according to the formula (II) are distinguished in that
G' represents
  a) hydroxyl,
  b) OZ',
  c) methoxy,
  d) ethoxy,
  e) tert-butoxy,
  f) isopropoxy, or
  g) O—$C_2H_4$—OMe.

Further preferred compounds of the invention according to the formula (II) are distinguished in that
G' represents
  a) hydroxyl,
  b) OZ',
  c) methoxy, or
  d) ethoxy.

Particularly preferred compounds of the invention according to the formula (II) are distinguished in that
G' represents
  a) hydroxyl,
  b) OZ', or
  c) methoxy.

Particularly preferred compounds of the invention according to the formula (II) are distinguished in that
G' represents ethoxy.

Preferred compounds of the invention according to the formula (II) are distinguished in that
$R^1$ and $R^2$ represent
  a) hydrogen,
  b) $^{18}F$,
  c) $^{18}F$-methoxy,
  d) $^{18}F$-ethoxy,
  e) $^{18}F$-propoxy,
  f) $^{18}F$-methyl,
  g) $^{18}F$-ethyl, or
  h) $^{18}F$-propyl,
with the proviso that exactly one of the substituents $R^1$ or $R^2$ contains exactly one $^{18}F$ isotope and the other substituent in each case is hydrogen.

Further preferred compounds of the invention according to the formula (II) are distinguished in that
$R^1$ and $R^2$ represent
  a) hydrogen,
  b) $^{18}F$,
  c) $^{18}F$-methoxy,
  d) $^{18}F$-methyl, or
  e) $^{18}F$-ethyl,
with the proviso that exactly one of the substituents $R^1$ or $R^2$ contains exactly one $^{18}F$ isotope and the other substituent in each case is hydrogen.

Particularly preferred compounds of the invention according to the formula (II) are distinguished in that
$R^1$ and $R^2$ represent
  a) hydrogen,
  b) $^{18}F$ or
  c) $^{18}F$-methyl,
with the proviso that exactly one of the substituents $R^1$ or $R^2$ contains exactly one $^{18}F$ isotope and the other substituent in each case is hydrogen.

Particularly preferred compounds of the invention according to the formula (II) are distinguished in that $R^1$ is selected from the group consisting of OH, $CH_3$, $C_2H_5$ and $C_3H_7$, and $R^2$ represents $^{18}F$.

Particularly preferred compounds of the invention according to the formula (II) are distinguished in that $R^2$ is selected from the group consisting of OH, $CH_3$, $C_2H_5$ and $C_3H_7$, and $R^1$ represents $^{18}F$.

Particularly preferred compounds of the invention according to the formula (II) are distinguished in that $R^1$ represents H and $R^2$ represents $^{18}F$.

Particularly preferred compounds of the invention according to the formula (II) are distinguished in that $R^1$ represents $^{18}F$ and $R^2$ represents H.

Preferred compounds of the invention according to the formula (II) are distinguished in that Q represents
 a) N(H)-tert-butoxycarbonyl,
 b) N(H)-benzyloxycarbonyl,
 c) N-(tert-butoxycarbonyl)$_2$, or
 d)

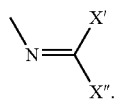

Further preferred compounds of the invention according to the formula (II) are distinguished in that Q represents
 a) N(H)-tert-butoxycarbonyl,
 b) N-(tert-butoxycarbonyl)$_2$, or
 c)

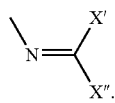

Particularly preferred compounds of the invention according to the formula (II) are distinguished in that Q represents
 a) N(H)-tert-butoxycarbonyl, or
 b)

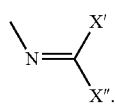

Particularly preferred compounds of the invention according to the formula (II) are distinguished in that Q represents N(H)-tert-butoxycarbonyl.

Particularly preferred compounds of the invention according to the formula (II) are distinguished in that Q represents

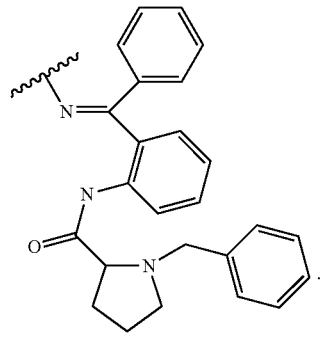 [SMILES: */N=C(\c1ccccc1)c1ccccc1NC(=O)C1CCCN1Cc1ccccc1]

Preferred compounds of the invention according to the formula (II) are distinguished in that
 L' represents
  a) methyl,
  b) ethyl,
  c) propyl,
  d) isopropyl,
  e) —$C_2H_4$—OMe, or
  f) —$C_2H_4$—O—$C_2H_4$—OMe.

Further preferred compounds of the invention according to the formula (II) are distinguished in that
 L' represents
  a) methyl, or
  b) ethyl.

Preferred compounds of the invention according to the formula (II) are distinguished in that
 U represents
  a) tert-butoxycarbonyl,
  b) allyloxycarbonyl, or
  c) ethoxycarbonyl.

Further preferred compounds of the invention according to the formula (II) are distinguished in that
 U represents
  a) tert-butoxycarbonyl, or
  b) ethoxycarbonyl.

Particularly preferred compounds of the invention according to the formula (II) are distinguished in that
 U represents
  tert-butoxycarbonyl.

Preferred compounds of the invention according to the formula (II) are distinguished in that
 X' and X" independently of one another represent
  a) branched or unbranched $C_1$-$C_5$ alkyl,
  b) substituted or unsubstituted aryl or
  c) aralkyl.

Further preferred compounds of the invention according to the formula (II) are distinguished in that
 X' and X" independently of one another represent
  a) branched or unbranched $C_1$-$C_5$ alkyl, or
  b) substituted or unsubstituted aryl.

Particularly preferred compounds of the invention according to the formula (II) are distinguished in that
 X' and X" represent phenyl or represent phenyl substituted in the 2-position.

Z' represents a metal cation equivalent, which can be mono- or divalent, where divalent metals can lead to ionic bonding with two radicals of the structures according to the invention or can form coordinative bonds with a carboxyl and amine function of the amino acid derivative, Preferred compounds of the invention according to the formula (II) are distinguished in that
Z' represents an $Ni^{2+}$ ion or
Z' is selected from the group consisting of: $Na^+$, $K^+$, $Ca^{2+}$ and $Mg^{2+}$,
where all possible diastereomers and enantiomers of the preferred compounds of the invention as set forth in formula (II) are part of the present subject of the invention.

Furthermore particularly preferred is any individual compound of the compounds from the following group where all possible diastereomers and enantiomers are part of the present subject of the invention:

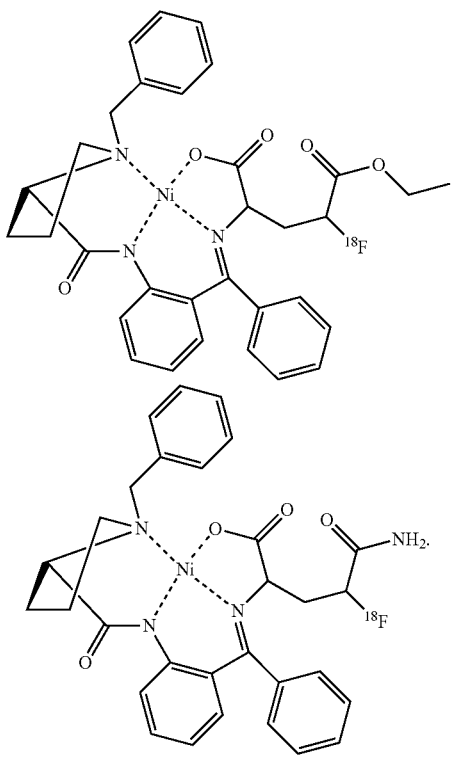

The process for the preparation of the compounds of the general formula (II) according to the invention is distinguished in that the majority of the compounds as set forth in formula (II) can be formed from a precursor compound of the compound of the formula (III) after introduction of the $^{18}F$ isotope.

In a third aspect, the present invention relates to compounds of the formula (III):

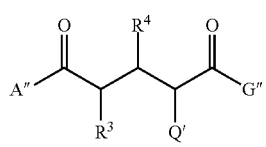

wherein
A" represents
a) hydroxyl,
b) branched or unbranched $C_1$-$C_5$ alkoxy,
c) branched or unbranched hydroxy $C_1$-$C_5$ alkoxy,
d) branched or unbranched O—$C_1$-$C_5$ alkyl-(O—$C_1$-$C_4$ alkyl)$_n$-O—$C_1$-$C_4$ alkyl,
e) $N(C_1$-$C_5$ alkyl)$_2$,
f) $NH_2$,
g) N(H)—U',
h) N(H)-L' or
i) O-L',
G" represents
a) hydroxyl,
b) O—Z",
c) branched or unbranched O—$C_1$-$C_5$ alkyl,
d) branched or unbranched O—$C_2$-$C_5$ alkenyl,
e) branched or unbranched O—$C_1$-$C_5$ alkyl-(O—$C_1$-$C_4$alkyl)$_n$-O—$C_1$-$C_4$alkyl,
f) branched or unbranched O—$C_2$-$C_5$ alkynyl, or
g) triphenylmethoxy,
$R^3$ and $R^4$ represent
a) hydrogen,
b) branched or unbranched E-$C_1$-$C_5$ alkoxy,
c) branched or unbranched E-$C_1$-$C_5$ alkyl,
d) branched or unbranched E-hydroxy-$C_1$-$C_5$-alkyl,
e) branched or unbranched E-$C_2$-$C_5$ alkenyl,
f) branched or unbranched E-$C_2$-$C_5$ alkynyl,
g) hydroxyl,
h) branched or unbranched $C_1$-$C_5$ alkyl, or
i) branched or unbranched $C_1$-$C_5$ alkoxy,
with the proviso that exactly one of the substituents $R^3$ or $R^4$ contains an E and the other substituent in each case contains no E,
E represents
a) chloro,
b) bromo,
c) mesyloxy,
d) trifluoromesyloxy,
e) nonafluorobutyloxy, or
f) tosyloxy,
Q' represents
a) N(H)-tert-butoxycarbonyl,
b) N(H)-allyloxycarbonyl,
c) N(H)-benzyloxycarbonyl,
d) N(H)-ethoxycarbonyl,
e) N(H)-methoxycarbonyl
f) N(H)-propoxycarbonyl,
g) N(H)-2,2,2-trichloroethoxycarbonyl,
h) N(H)-1,1-dimethylpropynyl,
i) N(H)-1-methyl-1-phenylethoxycarbonyl,
j) N(H)-1-methyl-1-(4-biphenylyl)ethoxycarbonyl,
k) N(H)-cyclobutylcarbonyl,
l) N(H)-1-methylcyclobutylcarbonyl,
m) N(H)-vinylcarbonyl,
n) N(H)-allylcarbonyl,
o) N(H)-adamantylcarbonyl,
p) N(H)-diphenylmethylcarbonyl,
q) N(H)-cinnamylcarbonyl,
r) N(H)-formyl,
s) N(H)-benzoyl,
t) N(H)-trityl, u) N(H)-p-methoxyphenyldiphenylmethyl,
v) N(H)-di(p-methoxyphenyl)phenylmethyl, or
w)

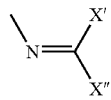

x) N-(tert-butoxycarbonyl)$_2$,
L" represents
  a) branched or unbranched $C_1$-$C_5$ alkyl,
  b) branched or unbranched $C_2$-$C_5$ alkenyl,
  c) branched or unbranched $C_1$-$C_5$ alkyl-(O—$C_1$-$C_4$ alkyl)$_n$-O—$C_1$-$C_4$ alkyl or
  d) branched or unbranched $C_2$-$C_5$ alkynyl,
U' represents
  a) tert-butoxycarbonyl,
  b) allyloxycarbonyl,
  c) benzyloxycarbonyl, or
  d) ethoxycarbonyl,
X' and X" independently of one another represent
  a) branched or unbranched $C_1$-$C_5$ alkyl,
  b) substituted or unsubstituted aryl,
  c) aralkyl or
  d) heteroaryl,
and
Z" represents a metal cation equivalent, which can be mono- or divalent, where divalent metals can lead to ionic bonding with two radicals of the structures according to the invention or can form coordinative bonds with a carboxyl and amine function of the amino acid derivative,
A preferred Z" is selected from the group consisting of Na$^+$, K$^+$, Ca$^{2+}$ and Mg$^{2+}$ or is Ni$^{2+}$,
where n is =0, 1 or 2 and all possible diastereomers and enantiomers are part of the present subject of the invention.
Preferred compounds of the invention according to the formula (III) are distinguished in that
A" represents
  a) hydroxyl,
  b) methoxy,
  c) ethoxy,
  d) tert-butoxy,
  e) NMe$_2$,
  f) NEt$_2$,
  g) NH$_2$,
  h) N(H)—U',
  i) N(H)-L" or
  j) O-L".
Further preferred compounds of the invention according to the formula (III) are distinguished in that
A" represents
  a) hydroxyl,
  b) methoxy,
  c) ethoxy,
  d) NMe$_2$,
  e) N(H)—U',
  f) NH$_2$, or
  g) N(H)-L".
Particularly preferred compounds of the invention according to the formula (III) are distinguished in that
A" represents
  a) hydroxyl,
  b) ethoxy,
  c) methoxy,
  d) N(H)—U, or
  e) NH$_2$.
Preferred compounds of the invention according to the formula (III) are distinguished in that
G" represents
  a) hydroxyl,
  b) OZ",
  c) methoxy,
  d) ethoxy,
  e) tert-butoxy,
  f) isopropoxy, or
  g) O—$C_2H_4$—OMe.
Further preferred compounds of the invention according to the formula (III) are distinguished in that
G" represents
  a) hydroxyl,
  b) OZ",
  c) methoxy, or
  d) ethoxy.
Particularly preferred compounds of the invention according to the formula (III) are distinguished in that
G" represents
  a) hydroxyl,
  b) OZ", or
  c) methoxy.
Preferred compounds of the invention according to the formula (III) are distinguished in that
$R^3$ and $R^4$ represent
  a) hydrogen,
  b) E-methoxy,
  c) E-ethoxy,
  d) E-propoxy,
  e) E-methyl,
  f) E-ethyl, or
  g) E-propyl,
with the proviso that exactly one of the substituents $R^3$ or $R^4$ contains an E and the other substituent in each case is hydrogen.
Further preferred compounds of the invention according to the formula (III) are distinguished in that
$R^3$ and $R^4$ represent
  a) hydrogen,
  b) E-methoxy,
  c) E-methyl, or
  d) E-ethyl,
with the proviso that exactly one of the substituents $R^3$ or $R^4$ contains an E and the other substituent in each case is hydrogen.
Particularly preferred compounds of the invention according to the formula (III) are distinguished in that
$R^3$ and $R^4$ represent
  a) hydrogen or
  b) E-methyl,
with the proviso that exactly one of the substituents $R^3$ or $R^4$ contains an E and the other substituent in each case is hydrogen.
Preferred compounds of the invention according to the formula (III) are distinguished in that
E represents
  a) chloro,
  b) bromo,
  c) mesyloxy,
  d) trifluoromesyloxy or
  e) tosyloxy.

Further preferred compounds of the invention according to the formula (III) are distinguished in that
E represents
a) chloro,
b) bromo,
c) mesyloxy,
d) trifluoromesyloxy or
e) tosyloxy.

Particularly preferred compounds of the invention according to the formula (III) are distinguished in that
E represents
a) bromo, or
b) mesyloxy.

Preferred compounds of the invention according to the formula (III) are distinguished in that
Q' represents
a) N(H)-tert-butoxycarbonyl,
b) N(H)-benzyloxycarbonyl, or
c)

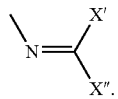

Further preferred compounds of the invention according to the formula (III) are distinguished in that
Q' represents
a) N(H)-tert-butoxycarbonyl, or
b)

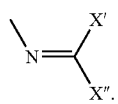

Preferred compounds of the invention according to the formula (III) are distinguished in that
L' represents
a) methyl,
b) ethyl,
c) propyl,
d) isopropyl,
e) —$C_2H_4$—OMe, or
f) —$C_2H_4$—O—$C_2H_4$—OMe.

Further preferred compounds of the invention according to the formula (III) are distinguished in that
L" represents
a) methyl, or
b) ethyl.

Preferred compounds of the invention according to the formula (III) are distinguished in that
U' represents
a) tert-butoxycarbonyl,
b) allyloxycarbonyl, or
c) ethoxycarbonyl.

Further preferred compounds of the invention according to the formula (III) are distinguished in that
U' represents
a) tert-butoxycarbonyl, or
b) benzyloxycarbonyl.

Particularly preferred compounds of the invention according to the formula (III) are distinguished in that
U' represents
tert-butoxycarbonyl.

Preferred compounds of the invention according to the formula (III) are distinguished in that
X' and X" independently of one another represent
a) branched or unbranched $C_1$-$C_5$ alkyl,
b) substituted or unsubstituted aryl, or
c) aralkyl.

Further preferred compounds of the invention according to the formula (III) are distinguished in that
X' and X" independently of one another represent
a) branched or unbranched $C_1$-$C_5$ alkyl, and
b) substituted or unsubstituted aryl.

Particularly preferred compounds of the invention according to the formula (III) are distinguished in that
X' and X" represent phenyl or represent phenyl substituted in the 2-position.

Preferred compounds of the invention according to the formula (III) are distinguished in that
Z" represents $Ni^{2+}$.

Where all possible diastereomers and enantiomers of the preferred compounds as set forth in formula (III) are part of the present subject of the invention.

The term "aryl", as it is applied here, standing by itself or as part of another group, relates to monocyclic or bicyclic aromatic groups which can contain six to twelve carbon atoms in the ring, such as, for example, phenyl or naphthyl, and can be arbitrarily substituted in position 2.

The aryl groups can be substituted in any suitable position which leads to a stable compound by one or more radicals from the group consisting of: hydroxyl, halogen, C1-C5-alkyl, C1-C5-alkoxy, cyano, CF3, nitro.

Substituents which may be mentioned are methoxy, ethoxy, propoxy, isopropoxy, hydroxyl, fluorine, chlorine, bromine, methyl, ethyl, propyl, isopropyl or trifluoromethyl groups.

Halogen is in each case to be understood as meaning fluorine, chlorine, bromine or iodine.

The term "alkyl", as it is applied here, standing by itself or as part of another group, relates to $C_1$-$C_6$-alkyl groups and can be straight-chain or branched and represents a methyl, ethyl, n-propyl, isopropyl, n-butyl, isobutyl, tert-butyl or n-pentyl, 2,2-dimethylpropyl, 2-methylbutyl or 3-methylbutyl group. A methyl or ethyl group is preferred.

Alkyl is in each case to be understood as meaning a straight-chain or branched alkyl radical, such as, for example, methyl, ethyl, propyl, isopropyl, butyl, isobutyl, sec-butyl, tert-butyl, pentyl, isopentyl or hexyl, heptyl, octyl, nonyl, decyl, undecyl, dodecyl.

The alkenyl substituents are in each case straight-chain or branched, the following radicals, for example, being meant: vinyl, propen-1-yl, propen-2-yl, but-1-en-1-yl, but-1-en-2-yl, but-2-en-1-yl, but-2-en-2-yl, 2-methylprop-2-en-1-yl, 2-methylprop-1-en-1-yl, but-1-en-3-yl, ethynyl, prop-1-yn-1-yl, but-1-yn-1-yl, but-2-yn-1-yl, but-3-en-1-yl, allyl.

The alkynyl groups can be straight-chain or branched and are, for example, C≡C, —$CH_2$—C≡CH, —C≡C—$CH_3$, —CH($CH_3$)—C≡CH, —C≡C—$CH_2$($CH_3$), —C($CH_3$)$_2$—C≡CH, —C≡C—CH($CH_3$)$_2$—, —CH($CH_3$)—C≡C—$CH_3$, —$CH_2$—C≡C—$CH_2$($CH_3$).

The $C_1$-$C_5$-alkoxy groups can be straight-chain or branched and represent a methoxy, ethoxy, n-propoxy, isopropoxy, n-butoxy, isobutoxy, tert-butoxy or n-pentoxy, 2,2-dimethylpropoxy, 2-methylbutoxy or 3-methylbutoxy group. A methoxy or ethoxy group is preferred.

The heteroaryl radical in each case comprises 5-16 ring atoms and instead of a carbon atom can contain one or more, identical or different heteroatoms, such as oxygen, nitrogen or sulfur in the ring, and can be mono-, bi- or tricyclic, and can additionally in each case be benzo-fused.

Examples which may be mentioned are:

thienyl, furanyl, pyrrolyl, oxazolyl, thiazolyl, imidazolyl, pyrazolyl, isoxazolyl, isothiazolyl, oxadiazolyl, triazolyl, thiadiazolyl, etc.

and benzo derivatives thereof, such as, for example, benzofuranyl, benzothienyl, benzothiazole, benzoxazolyl, benzimidazolyl, indazolyl, indolyl, isoindolyl, etc.;

or pyridyl, pyridazinyl, pyrimidinyl, pyrazinyl, triazinyl, etc. and benzo derivatives thereof, such as, for example, quinolyl, isoquinolyl, etc.;

or azocinyl, indolizinyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl.

The invention also comprises the $Ni^{2+}$ complex containing the Schiff's base of a compound as set forth in formula (I) and the compound (S)-2-[N—(N-benzylprolyl)amino]benzophenone as such and its use for the preparation of a compound as set forth in formula (I).

The invention further also comprises the $Ni^{2+}$ complex containing the Schiff's base of a precursor compound of the compound as set forth in formula (I) and the compound (S)-2-[N—(N-benzylprolyl)amino]benzophenone as such and its use for the preparation of a compound as set forth in formula (I).

Compounds according to the invention, such as, for example, 4-fluoro-I-glutamic acid and 4-fluoro-I-glutamine, can be prepared, for example, as in Scheme 1, by metal-catalyzed asymmetric synthesis with the aid of an $Ni^{2+}$ complex of a glycine-containing Schiff's base and (S)-2-[N—(N-benzylprolyl)amino]benzophenone (BPB) (1)[3] and ethyl ethyl-α-bromoacrylate or α-bromoacrylamide (2).

scheme 1

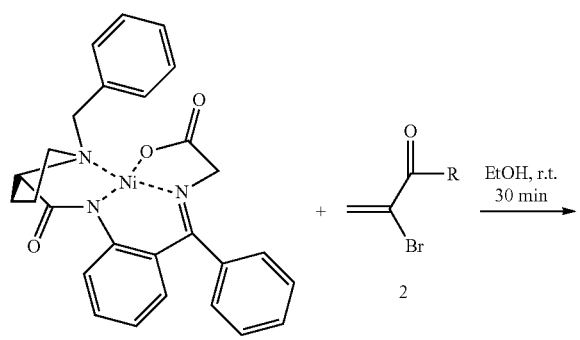

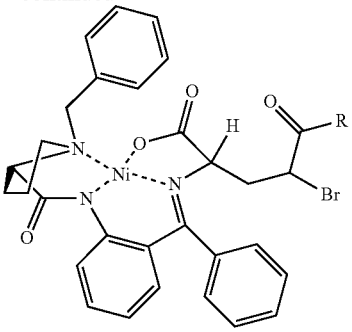

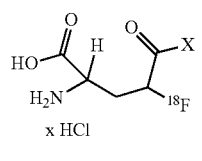

R = —OEt, —NH$_2$
X = —OH, —NH$_2$

Here, the C—C linkage can take place both in protic and aprotic solvents. The reaction can be carried out under mild conditions, such as, for example, room temperature, or elevated temperatures.

The addition of a base here is helpful. For instance, diisopropylamine, diisopropylethylamine, triethylamine or the like can be used. The reaction mixture is favorably stirred for 1-3 h and subsequently treated again with ethyl α-bromoacrylate or α-bromoacrylamide. The reaction can be monitored by means of TLC. Inter alia, silica gel/ethyl acetate/chloroform systems are suitable for this. After the addition of ethyl α-bromoacrylate or α-bromoacrylamide and stirring for at least 1 hour, the reaction is to a considerable extent complete. The reaction mixture is then neutralized by the addition of organic or mineral acid (or a combination of both), for example acetic acid, formic acid, trifluoroacetic acid, trichloroacetic acid, propionic acid, hydrochloric acid, sulfuric acid, perchloric acid, phosphoric acid etc. The ethyl 4-bromoglutamate-Ni complex can be separated from the reaction mixture by extraction. Suitable solvents for this are, for example, organic halogenated or nonhalogenated solvents, such as, for example, chloroform, methylene chloride, dialkyl ethers, ethyl acetate, alkanes, etc. After drying the organic phase by means of a drying agent (for example sodium sulfate, calcium sulfate or the like), the mixture is concentrated to dryness in vacuo.

By means of preparative TLC (for example on silica gel using an eluent mixture of AcOEt/CHCl$_3$, 1:1), a mixture of stereoisomeric complexes such as 3 (S,S,S) and 3 (S,R,S/R) can be detected. Complex 3 (S,S,R) can be separated, for example, in the aforementioned separation system with an R$_f$ of 0.49. The complexes 3 can be eluted from the silica gel, for example, using MeOH, EtOH etc. and subsequently purified by column chromatography, for example on Sephadex using EtOH/C$_6$H$_6$ mixtures.

The complex obtained can then be employed for further substitution reactions on the carbon atom substituted by bromine.

The precursor compound 3 according to the invention can be converted to the corresponding fluorinated precursor compound 4 by nucleophilic substitution by [$^{18}$F]F$^-$. For this, the complexes 3 can be reacted in the presence of a base such as, for example, NBu$_4$OH, (NBu$_4$)$_2$CO$_3$, K$_2$CO$_3$ etc. with the appropriate fluoride solution. The reaction preferably proceeds at elevated temperatures. The addition of crown ethers, such as, for example, Kryptofix (K2.2.2), can positively influence the reaction, particularly in combination with K$_2$CO$_3$ as a catalyzing base.

The fluorinated compounds 4-fluoroglutamic acid or 4-fluoroglutamine can be released from the corresponding complexes 3 by treatment with acids, such as, for example, hydrochloric acid, phosphoric acid, perchloric acid, sulfuric acid etc. Here, both the cleavage of the amino acid derivative and the cleavage of the ester in the 5-position occurs when using 5-methyl 4-fluoroglutamate.

4-Fluoroglutamic acid can be prepurified by means of a cartridge (for example QMA (Waters), LiChrolut (VWR/Merck) or WHAT6803-2005 SPE COLSAX (VWR/Merck)). The separation of impurities (complex compound 3,4,4-bromoglutamic acid etc.) can be carried out by means of HPLC. Suitable HPLC systems can, for example, be: column: amino group-bearing silica gel (for example Zorbax-NH$_2$); eluent: 20 mM NaH$_2$PO$_4$ in water, flow: 4 ml/min. The purified compound 5 can be concentrated by suitable removal of the HPLC solvents and employed for use for the purposes of this invention. The removal of the HPLC solvents can be carried out in different ways. Concentration on a rotary evaporator under reduced pressure, heating of the sample in a heating block under a stream of nitrogen etc. or application to a concentrator cartridge (for example C-18 SepPack etc), followed by elution with a little EtOH/aqueous sodium chloride solution or the like with subsequent further concentration by the aforementioned methods is suitable.

Compounds according to the invention, in which the [F-18] isotope is likewise positioned in the 4-position of the glutamic acid structure (5), can also be prepared as shown in Scheme 2. Thus, the acidic cleavage of the protective groups of the compound 6 takes place by way of example in order to obtain the compound 4-fluoromethylglutamic acid (5) according to the invention.

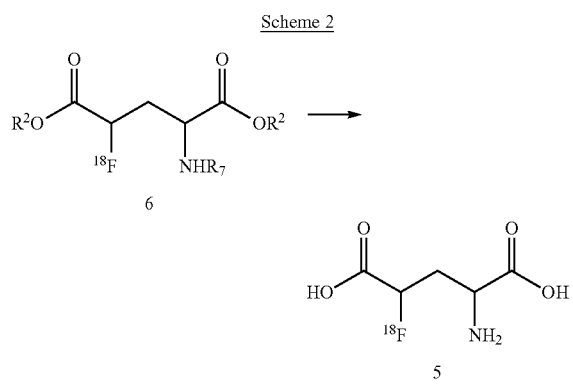

R$^2$ = ——Me; ——Et; t-Bu
R$^7$ = protective group, for example, Boc, trityl, acetyl Here, various organic acids (for example trifluoroacetic acid), but especially inorganic acids such as, for example, hydrobromic acid, hydrochloric acid, sulfuric acid, perchloric acid or phosphoric acid can be used. The purification of the compound 5 according to the invention as set forth in formula (I) is possible by HPLC, where various purification steps can in principle be inserted upstream and inserted downstream, such as, for example, purification by means of an RP-C18 cartridge or other separating materials.

The radiochemical fluorination of tosylate 7, whose synthesis took place from 8 (N. Sharma et al. Tetrahedron Lett. 2004, 45, 1403-1406) analogously to the method described in the literature (X. Zhang Tetrahedron Lett. 2001, 42, 5335-5338), to give the [F-18]-labeled glutamic acid derivative 6 is feasible according to the methods known to the person skilled in the art (see Scheme 3).

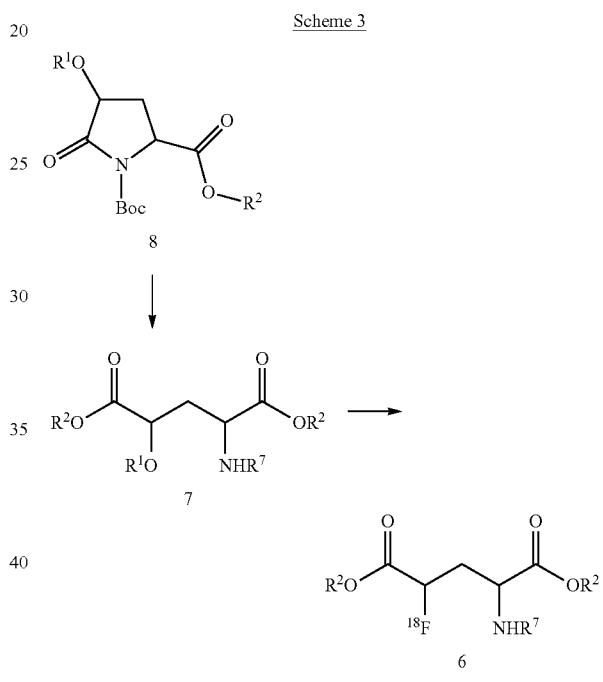

R$^1$ = leaving group, e.g. Ms, Tf, Ts
R$^2$ = Me, Et, $^t$Bu
R$^7$ = protective group, e.g. Boc, Fmoc Here, compound 7 can be reacted with the appropriate [F-18] fluoride solution in the presence of a base such as, for example, tetraalkylammonium and tetraalkylphosphonium carbonate and potassium carbonate etc. The reaction preferably proceeds at elevated temperatures. The addition of crown ethers, such as, for example, Kryptofix (K2.2.2), can positively influence the reaction, particularly in combination with K$_2$CO$_3$ as a catalyzing base. Possible solvents are preferably aprotic, but protic solvents or else aprotic solvent additives, such as, for example, water, can also be used. Customarily, acetonitrile, dimethyl sulfoxide or dimethylformamide are used as optimal solvents for the radiochemical fluorination with [F-18] fluoride anions. Compounds according to the invention such as 6 can be purified by HPLC and/or cartridges, where various purification steps can in principle be inserted upstream and inserted downstream, such as, for example, purification by means of an RP-C18 cartridge or other separating materials.

The preparation of the F-19 reference compounds 10 and 11 takes place as shown in Scheme 4.

Scheme 4

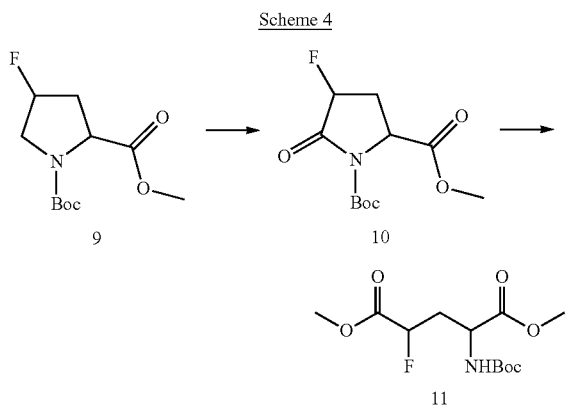

For instance, 10 can be prepared by oxidation of the fluoroproline derivative 9. The open-chain reference substance 11 can be obtained by ring opening of 10.

Furthermore, compounds according to the invention such as 5 can also be prepared directly from the cyclic compound 8 (Scheme 3) using the fluorination conditions described. The cleavage of the protective groups or the ring opening can be carried out analogously to the conditions for the removal of acidic protective groups (Scheme 2). For this purpose, various organic acids (for example trifluoroacetic acid), but especially inorganic acids such as, for example, hydrobromic acid, hydrochloric acid, sulfuric acid, perchloric acid or phos- Compounds according to the invention, in which the [F-18] isotope is positioned in the β-position, such as, for example, in the case of 3-fluoroglutamic acid (12), can be prepared as shown in Scheme 5. Thus the acidic cleavage of the protective groups of the compound 13 succeeds by way of example in order to obtain the compound according to the invention 3-fluoroglutamic acid (12).

Scheme 5

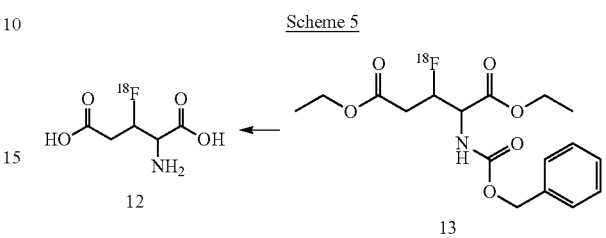

Here, various organic, but especially inorganic, acids such as, for example, hydrobromic acid, hydrochloric acid, sulfuric acid, perchloric acid or phosphoric acid can be used. Cleavage of the protective groups under strongly basic conditions using, for example, sodium hydroxide solution or potassium hydroxide solution is less favorable, but also utilizable and feasible in principle. The purification of the compound 12 according to the invention as set forth in formula (I) is possible by HPLC, where various purification steps can in principle be inserted upstream and inserted downstream, such as, for example, purification by means of an RP-C18 cartridge or other separating materials.

The radiochemical fluorination of tosylate 14, whose synthesis is described in the literature (Chem. Pharm. Bull., 17, 5, (1969), 879-885), to give the [F-18]-labeled glutamic acid derivative 13 is feasible according to the methods known to the person skilled in the art (see Scheme 6).

Scheme 6

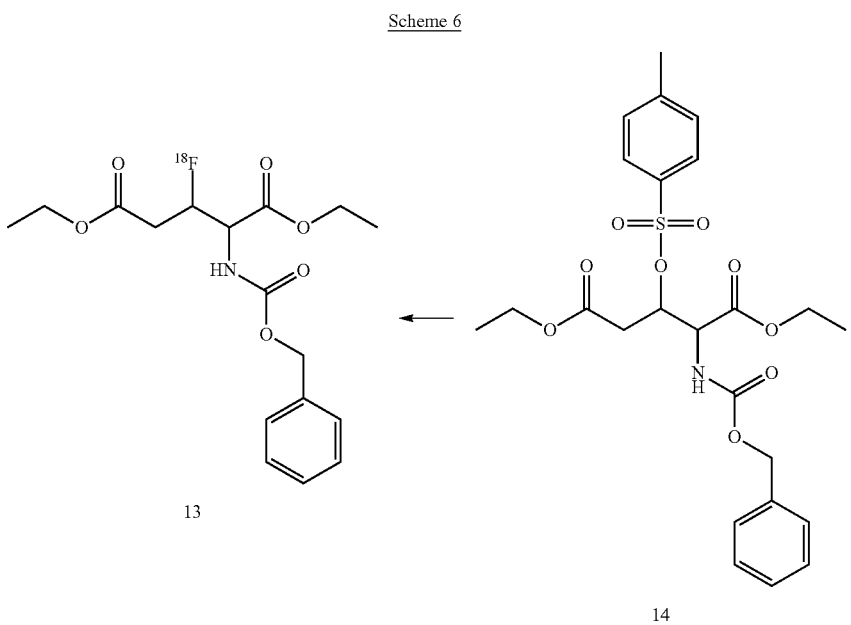 [SMILES: CCOC(=O)CC([18F])C(NC(=O)OCc1ccccc1)C(=O)OCC ; CCOC(=O)CC(OS(=O)(=O)c1ccc(C)cc1)C(NC(=O)OCc1ccccc1)C(=O)OCC]

phoric acid can be used. Furthermore, basic ring opening is also possible using lithium hydroxide, sodium hydroxide, potassium hydroxide etc. (S. Baker et al. *Tetrahedron Lett.* 1998, 39, 2815-2818).

Here, compound 14 can be reacted with the appropriate [F-18] fluoride solution in the presence of a base such as, for example, tetraalkylammonium and tetraalkylphosphonium carbonate and potassium carbonate etc. The reaction preferably proceeds at elevated temperatures. The addition of crown ethers, such as, for example, Kryptofix (K2.2.2), can positively influence the reaction, particularly in combination with K₂CO₃ as a catalyzing base. Possible solvents are preferably aprotic, but protic solvents or else aprotic solvent additives, such as, for example, water, can also be used. Customarily, acetonitrile, dimethyl sulfoxide or dimethylformamide are used as optimal solvents for the radiochemical fluorination with [F-18] fluoride anions. Compound 13 customarily does not have to be subjected to purification, but can be treated immediately using the methods described for the reaction of 13 to 12. Purification of the compound 13 is, however, possible in principle, preferably by means of preparative HPLC using a nonpolar phase, such as, for example, RP C-18. Moreover, purification by means of cartridges is also possible.

Here, various organic acids (for example trifluoroacetic acid), but especially inorganic acids such as, for example, hydrobromic acid, hydrochloric acid, sulfuric acid, perchloric acid or phosphoric acid can be used. The purification of the compound according to the invention 16 as set forth in formula (I) is possible by HPLC, where in principle various purification steps can be inserted upstream and inserted downstream, such as, for example, purification by means of an RP-C18 cartridge or other separating materials.

The radiochemical fluorination of tosylate 17, the synthesis of which was carried out analogously to the method described in the literature (Chem. Pharm. Bull., 17, 5, (1969), 879-885) from 18 (Tetrahedron, 45, 5, (1989) 1453-1464), to give the [F-18]-labeled glutamic acid derivative 16 is feasible according to the methods known to the person skilled in the art (see Scheme 8).

Scheme 8

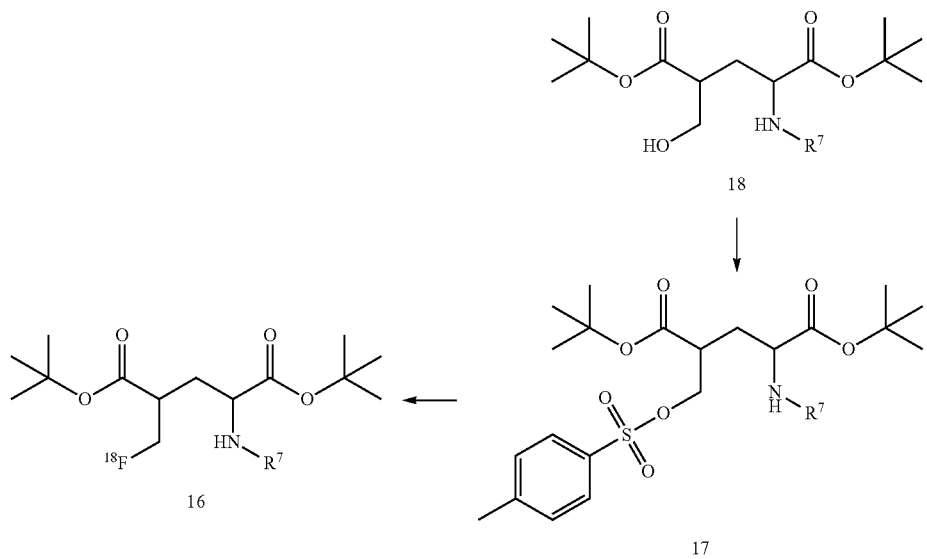

R⁷ = protective group, e.g. trityl, Boc

Compounds according to the invention in which the [F-18] isotope is positioned in the 4-position of the glutamic acid structure by means of a methylene group, such as, for example, in the case of 4-[F-18]fluoromethylglutamic acid (15), can be prepared as shown in Scheme 7. Thus, by way of example, the acidic cleavage of the protective groups of the compound 16 succeeds in order to obtain the compound according to the invention 4-[F-18]fluoromethylglutamic acid (15).

Scheme 7

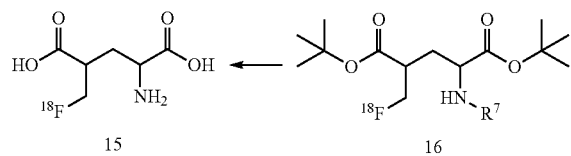

R⁷ = protective group, e.g. trityl, Boc, etc.

Here, compound 17 can be reacted with the appropriate [F-18] fluoride solution in the presence of a base such as, for example, tetraalkylammonium and tetraalkylphosphonium carbonate and potassium carbonate etc. The reaction preferably proceeds at elevated temperatures. The addition of crown ethers, such as, for example, Kryptofix (K2.2.2), can positively influence the reaction, particularly in combination with K₂CO₃ as a catalyzing base. Possible solvents are preferably aprotic solvents, but protic solvents or else aprotic solvent additives, such as, for example, water, can also be used. Customarily, acetonitrile, dimethyl sulf oxide or dimethylformamide are used as optimal solvents for the radiochemical fluorination with [F-18] fluoride anions. Compound 16 customarily does not have to undergo purification, but can be treated immediately using the methods described for the reaction of 16 to 15. Purification of the compound 16 is, however, possible in principle, preferably by means of preparative HPLC using a nonpolar phase, such as, for example, RP C-18.

Compounds according to the invention in which the [F-18] isotope is positioned in the 4-position of the glutamic acid structure by means of an alkoxy group, such as, for example, in the case of 4-[F-18]fluoroethoxyglutamic acid (20), can be prepared as shown in Scheme 9. Thus the acidic cleavage of the protective groups of the compound 21 or 22 succeeds by way of example in order to obtain the compound according to the invention 4-[F-18]fluoroethoxyglutamic acid (20).

Scheme 9

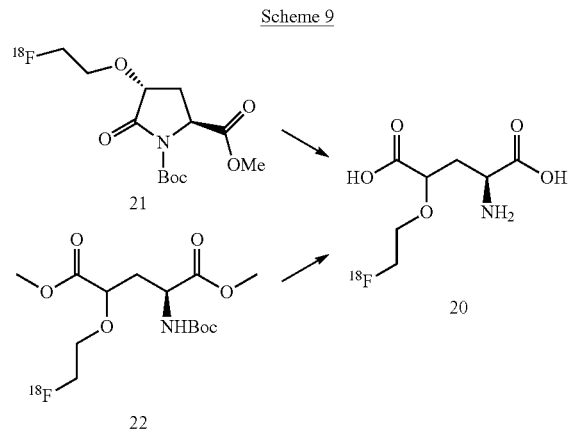

Here, various organic acids (for example trifluoroacetic acid), but especially inorganic acids such as, for example, hydrobromic acid, hydrochloric acid, sulfuric acid, perchloric acid or phosphoric acid can be used. Furthermore, basic ring opening of 21 is also possible using lithium hydroxide, sodium hydroxide, potassium hydroxide etc. (S. Baker et al. *Tetrahedron Lett.* 1998, 39, 2815-2818.)

The purification of the compound according to the invention 20 as set forth in formula (I) is possible by HPLC, where various purification steps can in principle be inserted upstream and inserted downstream, such as, for example, purification by means of an RP-C18 cartridge or other separating materials.

The radiochemical fluorination of tosylate 23 whose synthesis was carried out from 24 analogously to the method described in the literature (N. Sharma et al. *Tetrahedron Lett.* 2004, 45, 1403-1406.) to give the [F-18]-labeled glutamic acid derivative 21 is feasible according to the methods known to the person skilled in the art (see Scheme 10).

Scheme 10

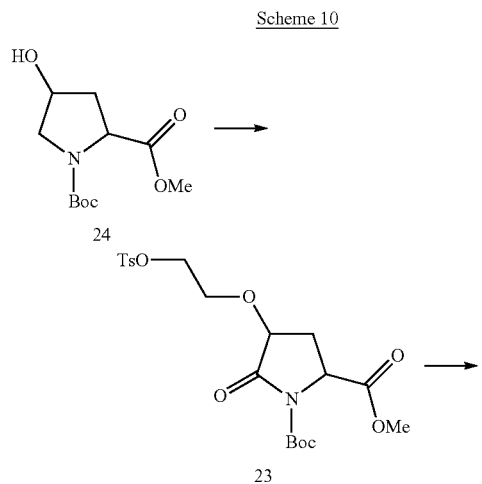

-continued

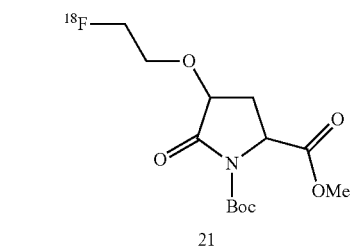

Here, compound 21 can be reacted with the appropriate [F-18] fluoride solution in the presence of a base such as, for example, tetraalkylammonium and tetraalkylphosphonium carbonate and potassium carbonate etc. The reaction preferably proceeds at elevated temperatures. The addition of crown ethers, such as, for example, Kryptofix (K2.2.2), can positively influence the reaction, particularly in combination with $K_2CO_3$ as a catalyzing base. Possible solvents are preferably aprotic solvents, but protic solvents or else aprotic solvent additives, such as, for example, water, can also be used. Customarily, acetonitrile, dimethyl sulfoxide or dimethylformamide are used as optimal solvents for the radiochemical fluorination with [F-18] fluoride anions. Compound 21 customarily does not have to be subjected to purification, but can be treated immediately using the methods described for the reaction of 21 to 20. Purification of the compound 21 is, however, possible in principle, preferably by means of preparative HPLC using a nonpolar phase, such as, for example, RP C-18. Moreover, purification by means of cartridges is possible.

The radiochemical fluorination of tosylate 25, whose synthesis was carried out from 23 analogously to the method described in the literature (X. Zhang *Tetrahedron Lett.* 2001, 42, 5335-5338), to give the [F-18]-labeled glutamic acid derivative 22 is feasible according to the methods known to the person skilled in the art (see Scheme 11).

Scheme 11

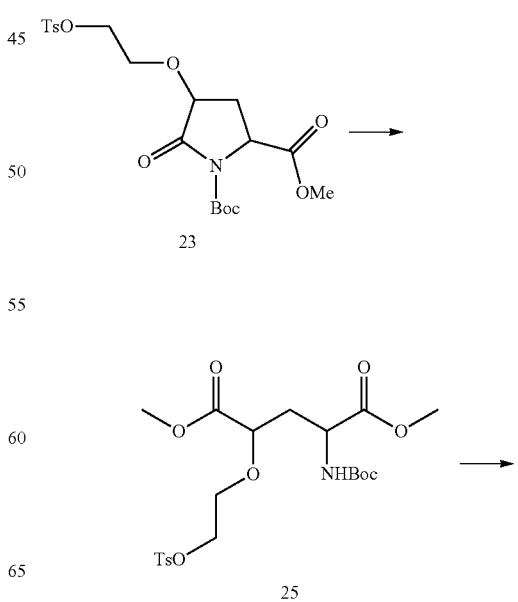

29

-continued

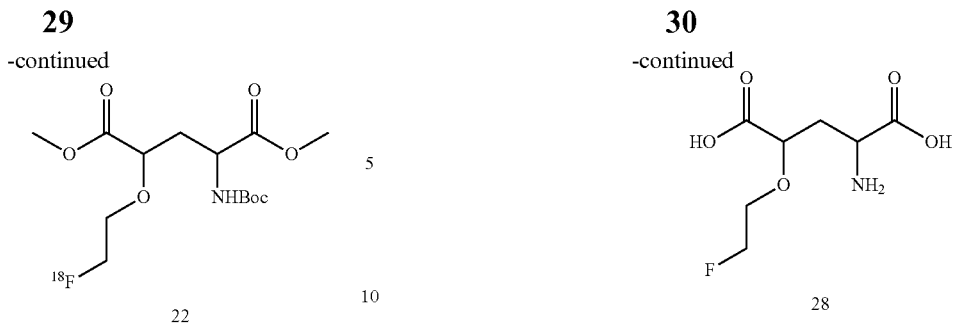

22

Here, compound 25 can be reacted with the appropriate [F-18] fluoride solution in the presence of a base such as, for example, tetraalkylammonium and tetraalkylphosphonium carbonate and potassium carbonate etc. The reaction preferably proceeds at elevated temperatures. The addition of crown ethers, such as, for example, Kryptofix (K2.2.2), can positively influence the reaction, particularly in combination with $K_2CO_3$ as a catalyzing base. Possible solvents are preferably aprotic, but protic solvents or else aprotic solvent additives, such as, for example, water, can also be used. Customarily, acetonitrile, dimethyl sulfoxide or dimethylformamide are used as optimal solvents for the radiochemical fluorination with [F-18] fluoride anions. Compound 22 customarily does not have to undergo purification, but can be treated immediately using the methods described for the reaction of 22 to 20. Purification of the compound 22 is, however, possible in principle, preferably by means of preparative HPLC using a nonpolar phase, such as, for example, RP C-18. Moreover, purification by means of cartridges is possible.

The synthesis of F-19 reference compounds 26, 27 and 28 can be carried out as shown in Scheme 12.

30

-continued

28

26 can be obtained by alkylation and oxidation of the hydroxyproline derivative 24. By ring opening of the pyroglutamine derivative 26, the open-chain reference compound 27 is obtained. The acidic cleavage of the protective groups leads to the glutamic acid derivative 28.

Compounds according to the invention in which the [F-18] isotope is positioned in the 4-position of the glutamic acid structure by means of an alkyl group, such as, for example, in the case of 4-[F-18]fluoropropylglutamic acid (29) or 4-[F-18]fluorobutylglutamic acid (30) can be prepared as shown in Scheme 13. Thus, the acidic cleavage of the protective groups of the compounds 31 and 32 succeeds by way of example, in order to obtain the compound 4-[F-18]fluoropropylglutamic acid (29) or 4-[F-18]fluorobutylglutamic acid (30) according to the invention.

Scheme 12

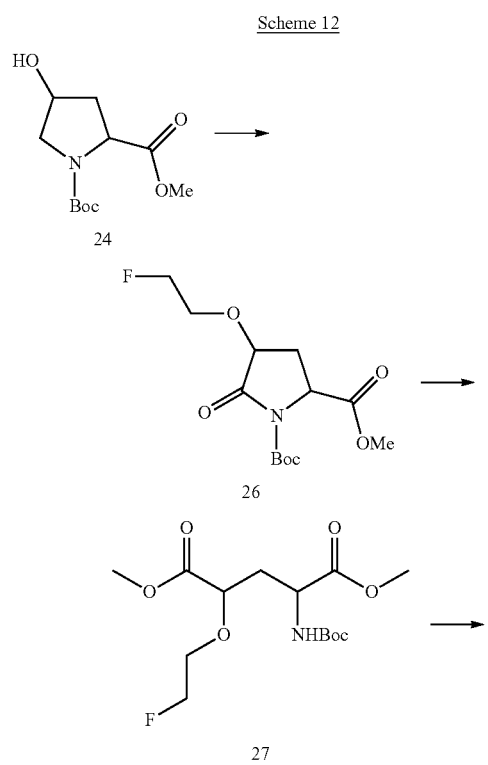

Scheme 13

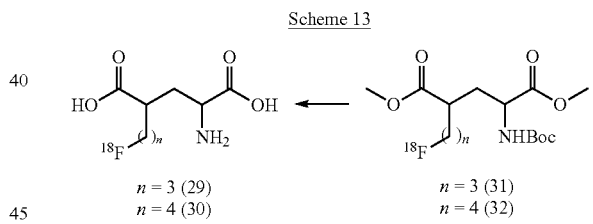

n = 3 (29)
n = 4 (30)

n = 3 (31)
n = 4 (32)

Here, various organic acids (for example trifluoroacetic acid), but especially inorganic acids such as, for example, hydrobromic acid, hydrochloric acid, sulfuric acid, perchloric acid or phosphoric acid can be used. The purification of the compound 29 and 30 according to the invention as set forth in formula (I) is possible by HPLC, where various purification steps can in principle be inserted upstream and inserted downstream, such as, for example, purification by means of an RP-C18 cartridge or other separating materials.

The radiochemical fluorination of bromide 33 or tosylate 34, whose synthesis was carried out from 35 analogously to the method described in the literature (S. Hanessian, et al. *J. Org. Chem.* 2005, 70, 5070-5085), to give the [F-18]-labeled glutamic acid derivatives 31 and 32 is feasible according to the methods known to the person skilled in the art (see Scheme 14).

Scheme 14

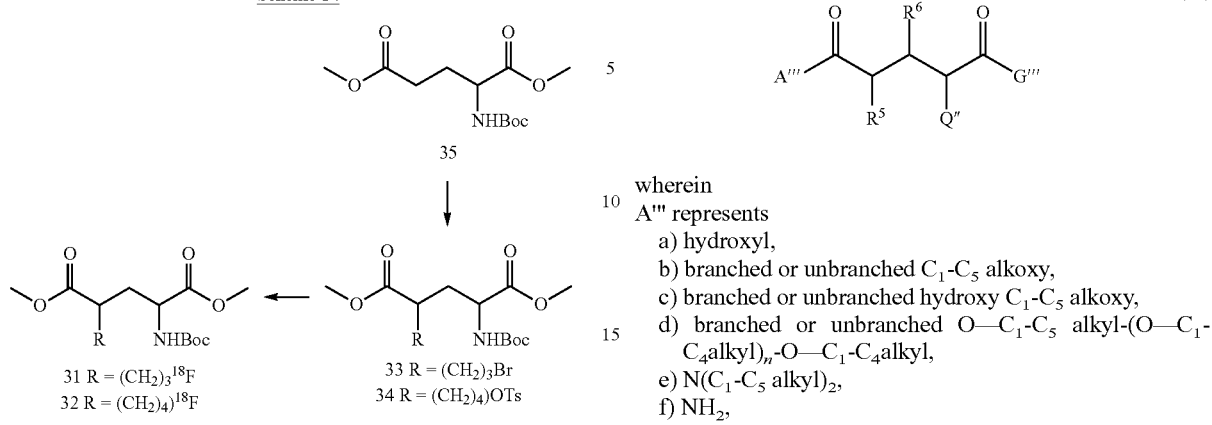

Here, the compounds 33 and 34 can be reacted with the appropriate [F-18] fluoride solution in the presence of a base such as, for example, tetraalkylammonium and tetraalkylphosphonium carbonate and potassium carbonate etc. The reaction preferably proceeds at elevated temperatures. The addition of crown ethers, such as, for example, Kryptofix (K2.2.2), can positively influence the reaction, particularly in combination with $K_2CO_3$ as a catalyzing base. Possible solvents are preferably aprotic solvents, but protic solvents or else aprotic solvent additives, such as, for example, water, can also be used. Customarily, acetonitrile, dimethyl sulfoxide or dimethylformamide are used as optimal solvents for the radiochemical fluorination with [F-18] fluoride anions. The compounds 31 and 32 customarily do not have to be subjected to purification, but can immediately be treated using the methods described for the reaction of 31 to 29 or 32 to 30. Purification of the compounds 31 and 32 is possible, however, in principle, preferably by means of preparative HPLC using a nonpolar phase, such as, for example, RP C-18.

The synthesis of the F-19 reference compounds 36 and 37 can be carried out by alkylation of the glutamic acid derivative 35 (Scheme 15).

Scheme 15

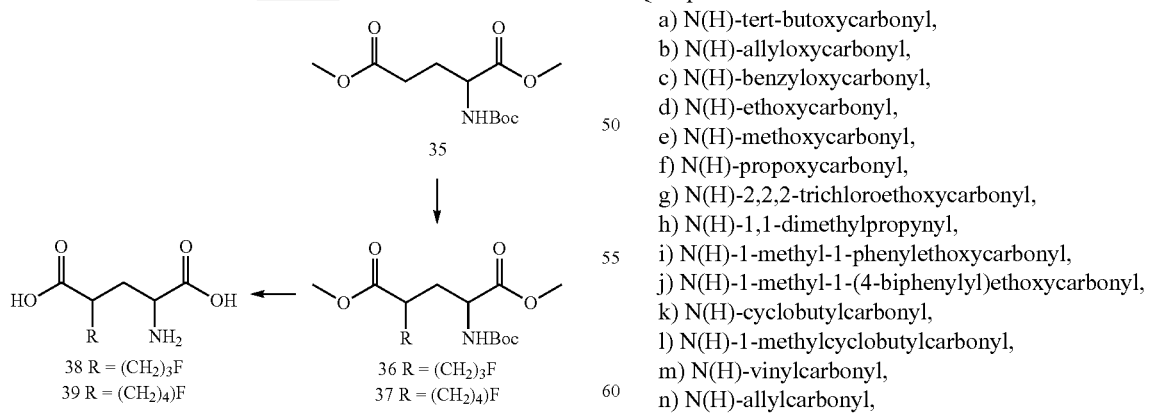

The cleavage of the protective groups leads to the fluoroalkylated glutamic acid derivatives 38 and 39.

In a fourth aspect of the invention, compounds of the formula (IV) are used for the preparation of compounds of the formula (I) or (II):

$$(IV)$$

wherein
A''' represents
  a) hydroxyl,
  b) branched or unbranched $C_1$-$C_5$ alkoxy,
  c) branched or unbranched hydroxy $C_1$-$C_5$ alkoxy,
  d) branched or unbranched O—$C_1$-$C_5$ alkyl-(O—$C_1$-$C_4$alkyl)$_n$-O—$C_1$-$C_4$alkyl,
  e) N($C_1$-$C_5$ alkyl)$_2$,
  f) $NH_2$,
  g) N(H)—U''',
  h) N(H)-L''' or
  i) O-L''',
G''' represents
  a) hydroxyl,
  b) branched or unbranched O—$C_1$-$C_5$ alkyl,
  c) branched or unbranched O—$C_2$-$C_5$ alkenyl,
  d) branched or unbranched O—$C_1$-$C_5$ alkyl-(O—$C_1$-$C_4$ alkyl)$_n$-O—$C_1$-$C_4$ alkyl or
  e) branched or unbranched O—$C_2$-$C_5$ alkynyl,
  f) triphenylmethoxy,
$R^5$ and $R^6$ represent
  a) hydrogen or
  b) E'',
with the proviso that exactly one of the substituents $R^5$ or $R^6$ contains an E' and the other substituent in each case contains no E',
E' represents
  a) chloro,
  b) bromo,
  c) mesyloxy,
  d) trifluoromesyloxy,
  e) nonafluorobutyloxy or
  f) tosyloxy,
Q'' represents
  a) N(H)-tert-butoxycarbonyl,
  b) N(H)-allyloxycarbonyl,
  c) N(H)-benzyloxycarbonyl,
  d) N(H)-ethoxycarbonyl,
  e) N(H)-methoxycarbonyl,
  f) N(H)-propoxycarbonyl,
  g) N(H)-2,2,2-trichloroethoxycarbonyl,
  h) N(H)-1,1-dimethylpropynyl,
  i) N(H)-1-methyl-1-phenylethoxycarbonyl,
  j) N(H)-1-methyl-1-(4-biphenylyl)ethoxycarbonyl,
  k) N(H)-cyclobutylcarbonyl,
  l) N(H)-1-methylcyclobutylcarbonyl,
  m) N(H)-vinylcarbonyl,
  n) N(H)-allylcarbonyl,
  o) N(H)-adamantylcarbonyl,
  p) N(H)-diphenylmethylcarbonyl,
  q) N(H)-cinnamylcarbonyl,
  r) N(H)-formyl,
  s) N(H)-benzoyl,
  t) N(H)-trityl, u) N(H)-p-methoxyphenyldiphenylmethyl,
v) N(H)-di(p-methoxyphenyl)phenylmethyl, or
w)

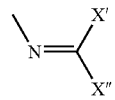

x) N-(tert-butoxycarbonyl)$_2$,

L''' represents
  a) branched or unbranched $C_1$-$C_5$ alkyl,
  b) branched or unbranched $C_2$-$C_5$ alkenyl,
  c) branched or unbranched $C_1$-$C_5$ alkyl-(O—$C_1$-$C_4$alkyl)$_n$-O—$C_1$-$C_4$alkyl, or
  d) branched or unbranched $C_2$-$C_5$ alkynyl, U'' represents
  a) tert-butoxycarbonyl,
  b) allyloxycarbonyl,
  c) benzyloxycarbonyl, or
  d) ethoxycarbonyl, X' and X'' independently of one another represent
  a) branched or unbranched $C_1$-$C_5$ alkyl,
  b) substituted or unsubstituted aryl,
  c) aralkyl, or
  d) heteroaryl where n is =0, 1, 2 or 3 and all possible diastereomers and enantiomers are part of the present subject of the invention.

The process for the preparation of the compounds of the general formula (I) or (II) according to the invention is distinguished in that the majority of the compounds as set forth in formula (I) or (II) can be formed from a precursor compound of the compounds of the formula (IV) after introduction of the $^{18}$F isotope.

The present invention relates to compounds of the general formula (IV).

In a fifth aspect of the invention, compounds of the formula (V) are used for the preparation of compounds of the formula (I) or (II):

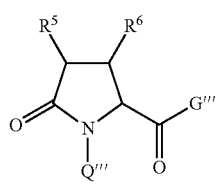

(V)

wherein
G''' represents
  a) hydroxyl,
  b) branched or unbranched O—$C_1$-$C_5$ alkyl,
  c) branched or unbranched O—$C_2$-$C_5$ alkenyl,
  d) branched or unbranched O—$C_1$-$C_5$ alkyl-(O—$C_1$-$C_4$alkyl)$_n$-O—$C_1$-$C_4$alkyl,
  e) branched or unbranched O—$C_2$-$C_5$ alkynyl, or
  f) triphenylmethoxy, $R^5$ and $R^6$ represent
  c) hydrogen or
  d) E', with the proviso that exactly one of the substituents $R^5$ or $R^6$ contains an E' and the other substituent in each case contains hydrogen, E' represents
  a) chloro,
  b) bromo,
  c) mesyloxy,
  d) trifluoromesyloxy,
  e) nonafluorobutyloxy or
  f) tosyloxy, Q''' represents
  a) N-tert-butoxycarbonyl,
  b) N-allyloxycarbonyl,
  c) N-benzyloxycarbonyl,
  d) N-ethoxycarbonyl,
  e) N-methoxycarbonyl,
  f) N-propoxycarbonyl,
  g) N-2,2,2-trichloroethoxycarbonyl,
  h) hydrogen,
  i) N-1-methyl-1-phenylethoxycarbonyl,
  j) N-1-methyl-1-(4-biphenylyl)ethoxycarbonyl,
  k) N-cyclobutylcarbonyl,
  l) N-1-methylcyclobutylcarbonyl,
  m) N-vinylcarbonyl,
  n) N-allylcarbonyl,
  o) N-adamantylcarbonyl,
  p) N-diphenylmethylcarbonyl,
  q) N-cinnamylcarbonyl,
  r) N-formyl, or
  s) N-benzoyl, where n is =0, 1, 2 or 3 and all possible diastereomers and enantiomers are part of the present subject of the invention.

The process for the preparation of the compounds of the general formula (I) or (II) according to the invention is distinguished in that the majority of the compounds as set forth in formula (I) or (II) can be formed from a precursor compound of the compounds of the formula (V) after introduction of the $^{18}$F isotope.

The present invention relates to compounds of the general formula (V).

Preferred compounds for the introduction of the $^{18}$F isotope are 4,7,13,16,21,24-hexaoxa-1,10-diazabicyclo[8.8.8]-hexacosane K18F (crown ether salt Kryptofix K18F),
K$^{18}$F,
H$^{18}$F,
KH$^{18}$F$_2$,
Cs$^{18}$F,
Na$^{18}$F or
$^{18}$F tetraalkylammonium salt (e.g. [F-18] tetrabutylammonium fluoride).

The present invention relates to compounds of the general formula (I) or (II) and processes where the fluorine isotopes $^{18}$F and $^{19}$F are used.

If one or more chiral centers is or are present in a compound of the present subject of the invention of the formula (I), formula (II), formula (III), formula (IV) or formula (V), all forms of this isomer, including both enantiomers and all possible diastereomers, should be contained herein. Compounds which contain at least one chiral center can be employed as a racemic mixture, optionally as a diastereomer or diastereomer-enriched mixture or as an enantiomer-enriched mixture. The racemic, enantiomer-enriched mixture or diastereomer mixture can optionally be separated according to the methods known to the person skilled in the art, so that the enantiomers or diastereomers can be employed individually. In those cases in which a carbon-carbon double bond is present, both "cis" and "trans" isomers are part of the present invention. In those cases in which tautomeric forms can be present, such as, for example, keto-enol tautomerism, all tautomeric forms are contained in the present invention, where these forms can be present in equilibrium or preferably in one form.

The compounds of the general formula I or II according to the invention and their preferred embodiments are used as medicaments.

The compounds of the general formula I or II according to the invention and their preferred embodiments are used in the diagnosis of physiological or pathological states.

Preferably, these compounds are used in noninvasive PET-based diagnosis on the human or animal body.

Particularly preferably, the compounds of the general formula I or II according to the invention and their preferred embodiments are used in the diagnosis of tumors. Examples of tumors of this type are malignant tumors of the gastrointestinal or colorectal tract, carcinoma of the liver, pancreas, kidney, bladder, thyroid gland, prostate, endometrium, ovary, testes, melanomocarcinoma, small-cell and non-small-cell bronchial carcinoma, dysplastic carcinoma of the oral mucosa, invasive oral cancer; breast cancer, including hormone-dependent and hormone-independent breast cancer, squamous epithelial carcinoma, neurological cancers including neuroblastoma, glioma, astrocytoma, osteosarcoma, meningioma; soft-tissue sarcoma; hemangioama and endocrine tumors, including hypophyseal adenoma, chromocytoma, paraganglioma, hematological tumors including lymphoma and leukemias; or metastases of one of the abovementioned tumors.

The compounds of the general formula I or II according to the invention and their preferred embodiments are used for the production of a medicament for the diagnosis of tumors. Examples of tumors of this type are malignant tumors of the gastrointestinal or colorectal tract, carcinoma of the liver, pancreas, kidney, bladder, thyroid gland, prostate, endometrium, ovary, testes, melanomocarcinoma, small-cell and non-small-cell bronchial carcinoma, dysplastic carcinoma of the oral mucosa, invasive oral cancer; breast cancer, including hormone-dependent and hormone-independent breast cancer, squamous epithelial carcinoma, neurological cancers including neuroblastoma, glioma, astrocytoma, osteosarcoma, meningioma, soft-tissue sarcoma; hemangioama and endocrine tumors, including hypophyseal adenoma, chromocytoma, paraganglioma, hematological tumors including lymphoma and leukemias; or metastases of one of the abovementioned tumors.

The invention relates to pharmaceutical preparations which contain at least one compound of the formula I or II and a pharmaceutically tolerable vehicle.

For the use of the compounds of the formula I or II as medicaments, these are brought into the form of a pharmaceutical preparation which, in addition to the active substance, contains pharmaceutical, organic or inorganic inert carrier materials suitable for enteral or parenteral administration, such as, for example, water, gelatin, gum arabic, lactose, starch, magnesium stearate, talc, vegetable oils, polyalkylene glycols etc.

The invention relates to an arrangement (kit) comprising at least one compound of the formula I, II, III, IV or V.

EXAMPLES

Example 1

Synthesis of 4-[F-18]fluoroglutamic acid

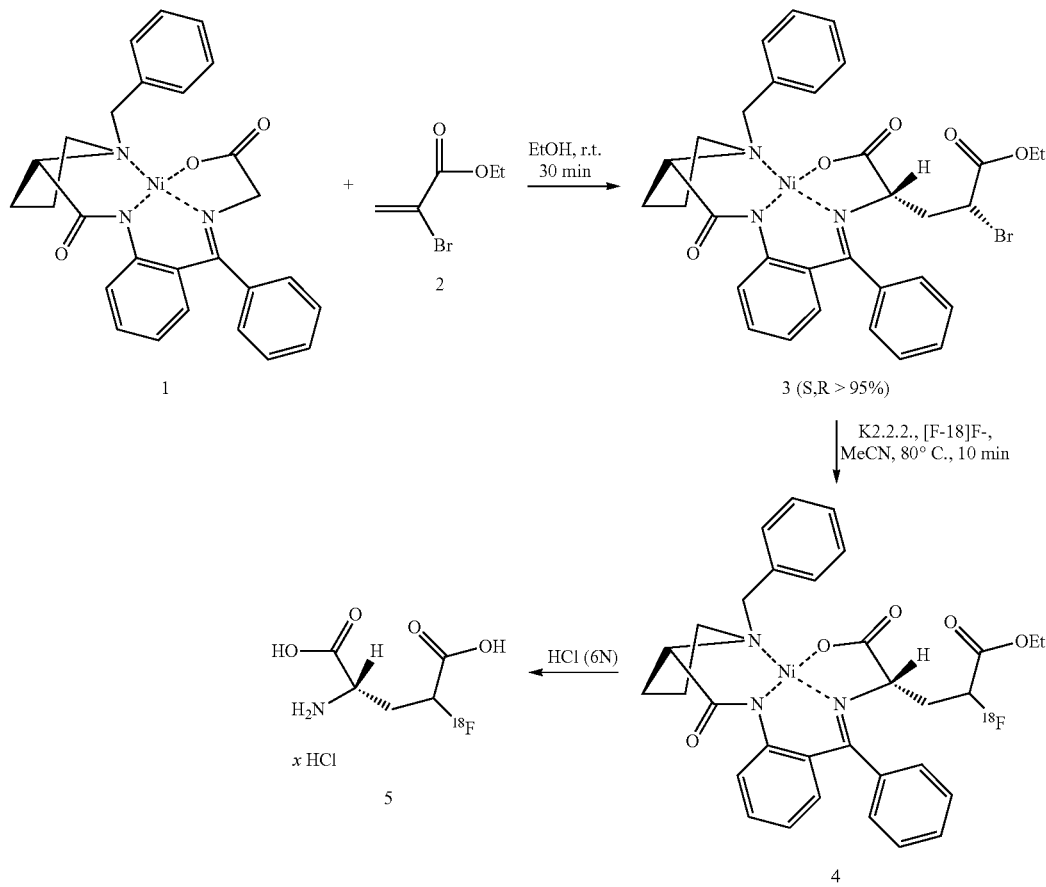

Synthesis of 3:

Diisopropylamine (0.031 ml, 0.22 mmol) was added to a suspension of complex 1 (0.1 g, 0.2 mmol) (*J. Am. Chem. Soc.*, 1985, 107, 4252 or *Tetrahedron Asymmetry*, 1998, 9, 4249) in EtOH (0.4 ml) at room temperature (RT). The reaction mixture was stirred for 30 min and subsequently treated with freshly distilled ester 2 (0.04 ml, 0.33 mmol) (*Gazz. Chim. Ital.*, 1981, 111, 249). The reaction was monitored by means of TLC ($SiO_2$, AcOEt/$CHCl_3$, 1:1). After completion of the reaction (~2.5 h), the reaction mixture was neutralized by the addition of AcOH (1.5 ml; 2%). After this, $CHCl_3$ (15 ml) was added, the mixture was washed with water (3×15 ml), and the organic phase was separated, dried over $Na_2SO_4$ and concentrated to dryness in vacuo. Preparative TLC ($SiO_2$, AcOEt/$CHCl_3$, 1:1) yielded a mixture of the complexes 3 (S,S,S) and 3 (S,R,S/R) in a ratio of 11:1 and a yield of 28% ($R_f$ 0.52). Complex 3 (S,S,R) showed an $R_f$ of 0.49. Complex 3 (S,S,R) was eluted from the silica gel using MeOH (3×40 ml) and subsequently purified by column chromatography on Sephadex using a 1:3 EtOH/$C_6H_6$ mixture. Purification yielded 0.052 g (52%) of product. Elemental analysis: found (%): C, 56.79; H, 4.85; Br, 12.14; N, 6.10; Ni, 8.17. $C_{32}H_{32}BrN_3NiO_5$. Calculated (%) C, 56.75; H, 4.76; Br, 11.80; N, 6.20; Ni, 8.67.

4-[F-19]Fluoro-L-Glutamic Acid (Nonradioactive Standard for HPLC Identification of 4-[F-18]Fluoro-L-Glutamic Acid)

Condensation of Ni-BPB-Gly with Ethyl 2-Fluoroacrylate.

1 ml (7.2 mmol) of i-$Pr_2NH$ was added at RT to a suspension of 3 g (6 mmol) of Ni-BPB-Gly in 15 ml of MeOH. The reaction mixture was stirred for 30 min and subsequently treated with 3.7 ml (30 mmol) of ethyl 2-fluoroacrylate. The progress of the reaction was monitored by means of TLC on $SiO_2$ (AcOEt/$CHCl_3$ (2:3)). After about 250 hours, the reaction was complete. After this, the mixture was neutralized by addition of 42 ml of a 2% strength aqueous solution of AcOH mixed with 25 ml of MeOH. The resulting mixture of the diastereoisomeric complexes of Ni-BPB-4-F-GluOMe was precipitated. The precipitate was filtered off and washed with water (3×30 ml). The resulting solid complex was suspended in $CCl_4$ and concentrated to dryness in vacuo. This procedure was repeated three times to free the mixture from water. The complexes were purified by column chromatography ($SiO_2$, 3×20 cm, AcOEt/$CHCl_3$, 3:2). The main fraction, 2.66 g, (4.4 mmol, 74%) contained a mixture of Ni-BPB-(2S,4R)-4-F-GluOMe and Ni-BPB-(2S,4S)-4-F-GluOMe in a ratio of 1.5/1. Melting point: 191-193° C. [α]D25+2477 (c 0.5, CHCl3). Elemental analysis: found (%): C, 61.76; H, 5.02; N, 6.94; Ni, 9.20. Calculated for $C_{31}H_{30}FN_3NiO_5$(%) C, 61.82; H, 5.02; N, 6.98; Ni, 9.74.

Separation of the complexes was achieved by column-chromatographic separation on Toyopearl HW-55F (column 2×50 cm, THF/$C_6H_6$ (2:7)).

Complex Ni-BPB-(2S,4R)-4-F-GluOMe: melting point: 207-208° C., $[\alpha]_D^{25}$+2617 (c 0.035, MeOH). Elemental analysis: found (%): C, 61.79; H, 4.95; N, 6.88. Calculated for $C_{31}H_{30}FN_3NiO_5$(%) C, 61.82; H, 5.02; N, 6.98.

Complex Ni-BPB-(2S,4S)-4-F-GluOMe. Melting point: 233-235° C., $[\alpha]_D^{25}$+2641 (c 0.039, MeOH). Elemental analysis: found (%): C, 61.63; H, 4.86; N, 6.84. Calculated for $C_{31}H_{30}FN_3NiO_5$(%) C, 61.82; H, 5.02; N, 6.98.

Decomposition of the Complex and Isolation of the Amino Acid.

2.75 g (4.57 mmol) of Ni-BPB-4-F-GluOMe complex were dissolved in 30 ml of MeOH in a round-bottomed flask and treated with stirring with 5.5 ml of HCl (6N). The reaction mixture was heated to reflux for 15-20 min, concentrated to dryness, diluted with 50 ml of water, and the hydro-chloride of the BPB was filtered off and carefully washed with 3×30 ml of water. The combined filtrates contain the amino acid, BPB residues and $Ni^{2+}$ salts and were adjusted to pH 5 with aqueous $NH_3$ solution. BPB residues were removed by extraction with $CHCl_3$ (3×30 ml). The combined aqueous phases were concentrated to dryness, treated with 3 ml of HCl (6N) and heated to reflux for 1 h. The solution was subsequently concentrated to dryness, dissolved in 5 ml of $H_2O$ and adjusted to pH 4 using 5% strength (aqueous) $NH_3$ solution. The amino acid was isolated by means of ion exchange chromatography on a Dowex column 50 w×8 in $H^+$ form (eluent: 5% $NH_3$ aq).

(2S,4R)-4-Fluoroglutamic acid: melting point: >300° C. (decomposition without melting point).

(2S,4S)-4-Fluoroglutamic acid: melting point: >300° C. (decomposition without melting point).

F-18 Radiolabeling:

Target: small-volume low-pressure silver target (1 ml) filled with [O-18] water for $^{18}O$ (p,n)$^{18}F$ reaction; cyclotron: Scanditronix MC 17; proton bombardment at 17 MeV.

F-18 fluoride was concentrated in a QMA resin cartridge (Waters, Sep Pak Light QMA Part No.: WAT023525) by application of the [F-18]/[O-18] target solution. The cartridge was preconditioned with $K_2CO_3$ solution (10 ml; 0.5 M) followed by deionized water (15 ml).

[F-18] radioactive complex: [F-18]Fluoride (15-300 mCi) was eluted from the QMA cartridge by means of wash solution (2 ml, MeCN (2 ml)/tetrabutylammonium carbonate (TBAC, 0.015 ml, 20% aqueous, pH 8)). The eluate was collected in a 5 ml vial and the solvents were removed by azeotropic distillation at 130° C. in a stream of nitrogen.

Nucleophilic substitution: The reaction vessel containing the dry [F-18] TBA fluoride was cooled to 80° C. (preceding step) and a solution of precursor 3 (S,S,R) (5 mg in MeCN (0.5 ml)) was added. The reaction mixture was kept at 80° C. for 5-10 min. A sample of the reaction mixture was investigated by means of radio-TLC (silica gel plate (Merck), eluent: ethyl acetate/chloroform/acetic acid (4/1/1). Based on these radio-TLC data, an incorporation of F-18 of 40-60% in 4 was determined.

Decomposition of the $^{18}F$-Fluorinated Ni Complex and Release of 4-[$^{18}F$]Fluoroglutamic Acid (A).

HCl (6 N, 0.3-0.5 ml) was added to the MeCN solution of the F-18 glutamate-nickel precursor and the mixture was treated at 140° C. for 5 min. A sample of the resulting reaction mixture was analyzed by means of radio-TLC (silica gel, eluent: n-butanol/acetic acid/water (12/3/5).

The TLC analysis was carried out on a MiniGita TLC scanner (Raytest, Germany).

Decomposition of the $^{18}F$-Fluorinated Ni Complex and Release of 4-[$^{18}F$]Fluoroglutamic Acid (B).

HCl (2 N, 0.3-0.5 ml) was added to the MeCN solution of the F-18 glutamate-nickel precursor and the mixture was treated at 140° C. for 5 min. Subsequently, it was neutralized with sodium hydroxide solution (2 N, 0.8-1.0 ml). A sample of the resulting reaction mixture was analyzed by means of radio-TLC (silica gel, eluent: n-butanol/acetic acid/water (12/3/5).

The TLC analysis was carried out on a MiniGita TLC scanner (Raytest, Germany).

Prepurification:

The crude product after the HCl treatment (previous step) was taken up in 1 ml of water and added to an anion exchange cartridge (Waters, SAX-OH form). 80% of the radioactive products were retained on the cartridge. The radioactive products were eluted from the cartridge by means of aqueous sodium chloride solution NaCl (0.4 M, 2 ml). A sample was analyzed by means of HPLC.

Identification by Radio-HPLC.

Pump: Gilson 305, injector: Rheodyne (20 µl injection loop), column: Zorbax-$NH_2$; 4.6×150 mm, mobile phase: $NaH_2PO_4$ (10 mM)/phosphoric acid, pH 3, flow: 1 ml/min, UV absorption detector: Gilson 116 in series with a Beckman 170 radiodetector, UV detection: 210 nm. $R_1$: F-19 reference ((rac)-4-F-Glu hydrochloride (diastereomer mixture: 1/5; described vide supra)): 12.22 min (UV); radioactivity detection (Beckman): 12.64 min. A single radioactive peak was obtained which coeluted with the reference compound.

Identification by radio-TLC: silica gel plate (mesh 60), eluent n-BuOH, AcOH, $H_2O$ (12:3:5). Detection: Phosphorimager: SI Molecular Dynamics. FIG. 1.

HPLC Purification:

pump: Gilson 305, injector: Rheodyne (20 µl injection loop), column: Zorbax-$NH_2$; 4.6×150 mm, mobile phase: $NaH_2PO_4$ (10 mM)/phosphoric acid, pH 3, flow: 1 ml/min, UV absorption detector: Gilson 116 in series with a Beckman 170 radiodetector, UV detection: 210 nm. An individual radioactive peak was obtained, which coeluted with the reference compound. If the resulting product is purified by means of HPLC, the prepurification by means of anion exchange cartridge described previously can be dispensed with.

It was possible to obtain the product with a radiochemical purity of >90% and a radioactivity of 15-200 mCi (corrected for disintegration).

Example 2

Synthesis of 2-amino-4-[F-19]fluoroglutamine (HPLC Standard)

Liquid ammonia (18 g) was added to a solution of 0.27 g (0.448 mmol) of Ni-BPB-4-F-GluOMe (M=602.28, prepared in analogy to Example 1) in 7 ml of MeOH. The reaction solution was left at RT for 2 h. The solution was concentrated in vacuo and the residue was purified by preparative TLC ($SiO_2$, $CHCl_3/Me_2CO$ (3:1)). After this, the product was further purified on Sephadex LH-20 ($C_6H_6$/EtOH (3:1). 0.15 g (0.255 mmol, 57%) of Ni-BPB-4-F-Gln (M.W. 587.28) was obtained.

Synthesis of 2-amino-4-[F-18]fluoroglutamine

[F-18]-Radioactive

Ni-BPB-4-F-GluOMe complex: [F-18]Fluoride (15-300 mCi) was eluted from the QMA cartridge by means of wash solution (2 ml, MeCN (2 ml)/tetrabutylammonium carbonate (TBAC, 0.015 ml, 20% aqueous, pH 8)). The eluate was collected in a 5 ml vial and the solvents were removed by azeotropic distillation at 130° C. in a stream of nitrogen.

Nucleophilic substitution: The reaction vessel containing the dry [F-18] TBA fluoride was cooled to 80° C. (preceding step) and a solution of precursor Ni-BPB-4-Br-GluOMe (5 mg in MeCN (0.5 ml)) was added. The reaction mixture was kept at 80° C. for 5-10 min. A sample of the reaction mixture was investigated by means of radio-TLC (silica gel plate (Merck), eluent: ethyl acetate/chloroform/acetic acid (4/1/1). Based on these radio-TLC data, an F-18 incorporation of 40-60% in Ni-BPB-4-F-GluOMe was determined.

[F-18]-Radioactive Ni-BPB-4-F-Gln Complex:

A mixture of 1 ml of t-BuOH and 1 g of dry $NH_3$ (dried over NaOH) was added to a solution of Ni-BPB-4-F-GluOMe (5-50 mCi) in 0.5 ml of t-BuOH. The reaction mixture was heated at 42° C. for 7 min until ester complex was no longer detectable (TLC, silica gel plate (Merck), eluent: ethyl acetate/chloroform/acetic acid (4/1/1)). The reaction proceeded quantitatively and yielded 4-40 mCi of Ni-BPB-4-F-Gln.

Decomposition of the $^{18}$F-Fluorinated Ni-BPB-4-F-Gln Complex and Release of 4-[$^{18}$F]Fluoroglutamic Acid HCl (2 N, 0.3-0.5 ml) was added to the MeCN solution of the [F-18] Ni-BPB-4-F-Gln nickel precursor and treated for 5 min at 140° C. Subsequently, the mixture was neutralized using sodium hydroxide solution (2 N, 0.8-1.0 ml). A sample of the resulting reaction mixture was analyzed by means of radio-TLC (silica gel, eluent: n-butanol/acetic acid/water (12/3/5).

The TLC analysis was carried out on a MiniGita TLC scanner (Raytest, Germany).

Prepurification:

The crude product after the HCl treatment (previous step) was taken up in 1 ml of water and added to an anion exchange cartridge (Waters, SAX-OH form). 70% of the radioactive products were retained in the cartridge. The radioactive products were eluted from the cartridge by means of aqueous sodium chloride solution NaCl (0.4 M, 2 ml). A sample was analyzed by means of HPLC.

Identification by Radio-HPLC.

Pump: Gilson 305, injector: Rheodyne (20 µl injection loop), column: Zorbax-$NH_2$; 4.6×150 mm, mobile phase: $NaH_2PO_4$ (10 mM)/phosphoric acid, pH 3, flow: 1 ml/min, UV absorption detector: Gilson 116 in series with a Beckman 170 radiodetector, UV detection: 210 nm. $R_r$: F-19 reference ((rac)-4-F-Gln hydrochloride: 8.04 min (UV); radioactivity detection (Beckman): 8.45 min. A single radioactive peak was obtained which coeluted with the reference compound.

HPLC Purification:

pump: Gilson 305, injector: Rheodyne (20 µl injection loop), column: Zorbax-$NH_2$; 4.6×150 mm, mobile phase: $NaH_2PO_4$ (10 mM)/phosphoric acid, pH 3, flow: 1 ml/min, UV absorption detector: Gilson 116 in series with a Beckman 170 radiodetector, UV detection: 210 nm. A single radioactive peak was obtained which coeluted with the reference compound. If the resulting product is purified by means of HPLC, the previously described prepurification by means of anion exchange cartridge can be dispensed with. It was possible to obtain the product with a radiochemical purity of >92% and a radioactivity of 3-31 mCi (corrected for decay).

Example 3

Synthesis of 2-amino-3-[F-18]fluoropentanedicarboxylic acid

[F-18] Fluoride-containing solution (33 µl, 789 MBq) was added to a mixture of 60 µl of aqueous 20% strength tetrabutylammonium carbonate solution in 1.5 ml of acetonitrile (1.0 ml). The solvent was removed by evaporating in a stream of nitrogen at an oven temperature of 120° C. 1 ml of anhydrous acetonitrile was added and removed again by evaporation. This last step was repeated again. A solution of 3 mg of diethyl 2-benzyloxycarbonylamino-3-(toluenesulfonyloxy)pentanedioate (Chem. Pharm. Bull., 17, 5, (1969), 879-885) in 0.3 ml of anhydrous acetonitrile was added to the residue and well stirred. After heating at 90° C. for 15 min, 2 ml of 40% strength aqueous hydrogen bromide solution were added. The reaction mixture was stirred at an oven temperature of 130° C. for 30 min and overpressure.

The crude product was analyzed radioanalytically by HPLC: pump: Gilson 305, injector: Rheodyne (20 μl injection loop), column: Zorbax-NH$_2$; 4.6×150 mm, mobile phase: NaH$_2$PO$_4$ (10 mM)/phosphoric acid, pH 3, flow: 1 ml/min, UV absorption detector: Gilson 116 in series with a Beckman 170 radiodetector, UV detection: 210 nm. $^{19}$F reference (J. Org. Chem.; 50; 17; (1985); 3163-3167). (UV); radioactivity detection (Beckman). A single radioactive peak was obtained, which coeluted with the reference compound.

The purification of the [F-18]-labeled compound was carried out by means of HPLC purification: pump: Gilson 305, injector: Rheodyne (20 μl injection loop), column: Zorbax-NH$_2$; 4.6×150 mm, mobile phase: NaH$_2$PO$_4$ (10 mM)/phosphoric acid, pH 3, flow: 1 ml/min, UV absorption detector: Gilson 116 in series with a Beckman 170 radiodetector, UV detection: 210 nm. A single radioactive peak was obtained, which eluted simultaneously with the $^{19}$F reference compound (J. Org. Chem.; 50; 17; (1985); 3163-3167). If the resulting product is purified by means of HPLC, the previously described prepurification by means of anion exchange cartridge can be dispensed with. It was possible to obtain the product with a radiochemical purity of about 92% and a radioactivity of 103 MBq.

Example 4

Di-t-butyl N-tritylglutamate

Triethylamine (40 ml) and trityl chloride (19.0 g, 68.5 mmol) were added to di-t-butylglutamic acid hydrochloride (20.0 g, 68 mmol, SIGMA, cat#: G-7501), dissolved in MeCl$_2$ (100 ml). The solution was stirred at room temperature for 24 h and subsequently washed with saturated sodium carbonate solution (3×) and water (3×). The organic phase was dried over MgSO$_4$, the solvent was removed in vacuo and the resulting orange-colored oil was purified by flash chromatography on silica gel in hexane/MeCl$_2$ (30/70). The white solid obtained contained the product accompanied by a residue of trityl-OH. The trityl alcohol was crystallized by dissolving the product mixture in a minimal amount of MeCl$_2$ and addition of hexane. After filtration and removal of the solvent mixture, a colorless oil was obtained. Yield: 6.0 g, (18%). TLC: Rf=0.5 (MeCl$_2$). Elemental analysis C$_{32}$H$_{39}$NO$_4$. found C, 76.4; H, 7.6; N, 2.9; calculated: C, 76.6; H, 7.8; N, 2.8.

t-Butyl 2-trityl-4-carbo-t-butyloxy-5-hydroxypentanoate n-Butyllithium (5.0 ml, 11 mmol) was added at 0° C. to a cyclohexylisopropylamine solution (3.0 ml, 15 mmol) in hexane (50 ml) in a three-necked flask. The solution was stirred at 0° C. for 30 min, subsequently cooled to −78° C. and treated with di-t-butyl N-tritylglutamate (5.0 g, 10 mmol) in hexane (50 ml). The flask was provided with a gas inlet tube and connected to a storage vessel, which contained paraformaldehyde and a gas inlet for argon. After the formation of the carbanion, the paraformaldehyde was heated to 180° C. and the resulting formaldehyde gas was led into the reaction vessel in a stream of argon for 30 min. In the course of this the bath temperature was kept at −78° C. Subsequently, the cooling bath was removed and the reaction mixture was slowly warmed to room temperature and filtered in order to remove paraformaldehyde residues. The filtrate was added to saturated aqueous ammonium chloride solution and extracted with diethyl ether (3×250 ml). The combined organic phases were dried using magnesium sulfate and the solvent was subsequently removed in vacuo. The resulting yellowish oil was purified by means of flash chromatography (ethyl acetate/MeCl$_2$ (10/90)). After removal of the solvent mixture, a colorless oil was obtained. Yield: 1.2 g, (25%). TLC: Rf=0.3 (MeCl$_2$). Elemental analysis C$_{33}$H$_{41}$NO$_5$. found C, 74.5; H, 7.6; N, 2.8; calculated: C, 74.6; H, 7.8; N, 2.6.

t-Butyl 2-trityl-4-carbo-t-butyloxy-5-toluoylsulfonic acid pentanoate t-Butyl 2-trityl-4-carbo-t-butyloxy-5-hydroxyheptanoate (532 mg, 1.00 mmol) was dissolved in MeCl$_2$ (6 ml) and pyridine (1.2 ml). Subsequently, p-toluenesulfonyl chloride (118 mg, 0.62 mmol) and dimethylaminopyridine (13.4 mg, 0.11 mmol) were added and the reaction mixture was stirred at room temperature overnight under a nitrogen atmosphere. The reaction mixture was extracted with ethyl acetate (3×), the combined organic phases were dried over sodium sulfate and filtered, and the solvents were removed on a rotary evaporator. The crude product was dissolved in a little MeCl$_2$, absorbed on NH$_2$ material and purified by means of column chromatography in ethyl acetate/hexane (8:2). Yield: 339 mg, (70%). Elemental analysis C$_{40}$H$_{47}$NO$_7$. found C, 70.3; H, 7.1; N, 2.2; S, 5.0 calculated: C, 70.1; H, 6.9; N, 2.0; S, 4.7.

t-Butyl 2-trityl-4-carbo-t-butyloxy-5-fluoropentanoate (HPLC reference)

Anhydrous tetrabutylammonium fluoride (102 mg, 0.4 mmol) was added to a solution of t-butyl 2-trityl-4-carbo-t-butyloxy-5-tolylsulfonic acid (2S)-heptanoate (54 mg, 0.08 mmol) in anhydrous THF (3 ml). The mixture was heated at reflux for 4 h. After the reaction mixture had been cooled to room temperature, the mixture was treated with MeCl$_2$ and subjected to aqueous extraction (3×). Preparative thin layer chromatography (MeCl$_2$/MeOH (90/10)) yielded the product as a yellowish oil. Yield: 22 mg, (51%). Elemental analysis C$_{33}$H$_{40}$NO$_4$. found C, 74.4; H, 7.7; N, 2.8; calculated: C, 74.3; H, 7.6; N, 2.6.

[F-18]-t-Butyl 2-trityl-4-carbo-t-butyloxy-5-fluoropentanoate

[F-18]Fluoride was prepared in a cyclotron by means of the [O-18](p,n)[F-18] reaction. The isotope solution was added to a Sep-Pack Light QMA cartridge and dried in a stream of air. The [F-18]fluoride was eluted from the cartridge using a Kryptofix 2.2.2/K$_2$CO$_3$ solution (22 mg of K2.2.2, 4.6 mg of K$_2$CO$_3$, 2 ml, MeCN (1.77 ml), water (0.23 ml)). The solvents were removed at 120° C. in a stream of argon. The residue was azeotropically distilled twice at 120° C. in a stream of argon with 1 ml of anhydrous MeCN. A solution of the tosylate precursor of t-butyl 2-trityl-4-carbo-t-butyloxy-5-tolylsulfonic acid (2S)-heptanoate (4 mg) in MeCN (0.2 ml) was added to a vessel containing the dried [F-18]fluoride. The reaction mixture was heated at 120° C. for 10 min. Subsequently, the solvent was removed in a stream of argon. The solvent (MeCN) was removed in a stream of nitrogen and the residue was treated with HCl (6 N, 0.3-0.5 ml) at 140° C. for 5 min. A sample of the resulting reaction mixture was analyzed by means of radio-TLC (silica gel, eluent: n-butanol/acetic acid/water (12/3/5).

The TLC analysis was carried out on a MiniGita TLC scanner (Raytest, Germany).

Prepurification:

The crude product after the HCl treatment (previous step) was taken up in 1 ml of water and added to an anion exchange cartridge (Waters, SAX-OH form). 80% of the radioactive products was retained on the cartridge. The radioactive products were eluted from the cartridge by means of aqueous sodium chloride solution NaCl (0.4 M, 2 ml). A sample was analyzed by means of HPLC.

Identification by Radio-HPLC.

Pump: Gilson 305, injector: Rheodyne (20 µl injection loop), column: Zorbax-$NH_2$; 4.6×150 mm, mobile phase: $NaH_2PO_4$ (10 mM)/phosphoric acid, pH 3, flow: 1 ml/min, UV absorption detector: Gilson 116 in series with a Beckman 170 radiodetector, UV detection: 210 nm. $R_f$: F-19 reference ((rac)-4-F-Glu hydrochloride): 14.53 min (UV); radioactivity detection (Beckman): 14.68 min. A single radioactive peak was obtained which coeluted with the reference compound.

HPLC Purification:

Pump: Gilson 305, injector: Rheodyne (20 µl injection loop), column: Zorbax-$NH_2$; 4.6×150 mm, mobile phase: $NaH_2PO_4$ (10 mM)/phosphoric acid, pH 3, flow: 1 ml/min, UV absorption detector: Gilson 116 in series with a Beckman 170 radiodetector, UV detection: 210 nm. A single radioactive peak was obtained which coeluted with the reference compound. If the resulting product is purified by means of HPLC, the previously described prepurification by means of anion exchange cartridge can be dispensed with. It was possible to obtain the product with a radiochemical purity of >90% and a radioactivity of 20-200 mCi (corrected for decay).

Example 5

Synthesis of 1-tert-butyl 2-methyl 4-methanesulfonyloxy-5-oxopyrrolidine-1,2-dicarboxylate (8a)

(according to N. Sharma et al. *Tetrahedron Lett.* 2004, 45, 1403-1406.) A solution of 15.29 g (71.5 mmol) of sodium periodate and 0.18 g (0.87 mmol) of ruthenium(III) chloride hydrate in 230 ml of water was added to 5.78 g (17.9 mmol) of Boc-gamma-MsO-proline methyl ester in 230 ml of ethyl acetate. The mixture was left at room temperature for three days with vigorous stirring. Subsequently, the phases were separated, the aqueous phase was extracted twice with ethyl acetate (80 ml) and the combined organic phases were stirred with 50 ml of isopropanol for 30 min. The mixture was dried over magnesium sulfate, filtered and the solvent was removed in vacuo. The crude product was purified by column chromatography (silica gel, hexane/ethyl acetate=6.5:3.5 to 5:5). 1.29 g (20%) of 1-tert-butyl 2-methyl 4-methanesulfonyloxy-5-oxopyrrolidine-1,2-dicarboxylate (8a) were obtained as a colorless solid.

Elemental analysis $C_{12}H_{19}NO_8S$. found C, 42.90; H, 5.68; N, 4.14; calculated: C, 42.73; H, 5.68; N, 4.15.

Synthesis of dimethyl 2-tert-butoxycarbonylamino-4-methanesulfonyloxypentane-dicarboxylate (7a)

(according to: X. Zhang *Tetrahedron Lett.* 2001, 42, 5335-5338.) 600 mg (1.78 mmol) of 1-tert-butyl 2-methyl 4-methanesulfonyloxy-5-oxopyrrolidine-1,2-dicarboxylate were dissolved in 7.5 ml of dichloromethane. 1.5 ml of methanol and 12.3 mg (0.089 mmol) of potassium carbonate were added. The resulting mixture was stirred at room temperature for three hours. Subsequently, the solvent was removed in vacuo and the crude product was purified by column chromatography (silica gel, dichloromethane/methanol=99.7:0.3 to 99.6:0.4). 608 mg (83%) of dimethyl 2-tert-butoxycarbonylamino-4-methanesulfonyloxypentanedicarboxylate (7a) were obtained as a colorless oil.

Elemental analysis $C_{13}H_{23}NO_9S$. found C, 42.10; H, 6.29; N, 3.69; calculated: C, 42.27; H, 6.28; N, 3.79.

F-18 Labeling of dimethyl 2-tert-butoxycarbonylamino-4-methanesulfonyloxypentane-dicarboxylate (7a)

[F-18]Fluoride was prepared in a cyclotron by means of the [O-18](p,n)[F-18] reaction. The isotope solution (2.47 GBq) was added to a Sep-Pack Light QMA cartridge. The [F-18] fluoride was eluted from the cartridge using a Kryptofix 2.2.21$K_2CO_3$ solution (5 g of K2.2.2, 1 mg of $K_2CO_3$, MeCN (1.5 ml), water (0.5 ml)). The solvent was removed at 120° C. in a stream of nitrogen with addition of acetonitrile (three times 1 ml).

5 mg (13.6 µmol) of dimethyl 2-tert-butoxycarbonylamino-4-methanesulfonyloxypentane-dicarboxylate (7a) in 1 ml of acetonitrile were added and the resulting mixture was stirred for 10 min at 100° C. After cooling to about 60° C., the mixture was added by means of a Silica-Plus cartridge.

The intermediate 6a was purified by HPLC (C18, acetonitrile/water). The HPLC fraction was diluted with water (about 50 ml) and added by means of a C18 cartridge. The intermediate was eluted with 1 ml of acetonitrile. 533 MBq (34% d.c.) of dimethyl 2-tert-butoxycarbonylamino-4-[F-18]fluoropentane dicarboxylate (6a) were obtained in a synthesis time of 64 min.

Synthesis of 4-[F-18]fluoroglutamic acid (5) by deprotection of dimethyl 2-tert-butoxycarbonylamino-4-[F-18]fluoropentanedicarboxylate (6a)

533 MBq of dimethyl 2-tert-butoxycarbonylamino-4-[F-18]fluoropentanedicarboxylate (6a) in 1 ml of acetonitrile were treated with 0.5 ml of 4N HCl. The mixture was heated for 5 min in an open vial with stirring at 140° C. (oil bath temperature). A further 0.5 ml of 4N HCl was added and the mixture was heated for 5 min in a closed vial with stirring at 140° C. (oil bath temperature).

After cooling to room temperature, the solution was neutralized by addition of about 1.5 ml of 2N NaOH.

It was possible to react dimethyl(2-tert-butoxycarbonylamino-4-[F-18]fluoropentane-dicarboxylate (6a) quantitatively (d.c.) to give 4-[F-18]fluoroglutamic acid (5).

Example 6

F-18 Labeling of 1-tert-butyl 2-methyl 4-methanesulfonyloxy-5-oxopyrrolidine-1,2-dicarboxylate (8a)

[F-18]Fluoride was prepared in a cyclotron by means of the [O-18](p,n)[F-18] reaction. The isotope solution (3.27 GBq) was added to a Sep-Pack Light QMA cartridge. The [F-18] fluoride was eluted from the cartridge using a Kryptofix 2.2.21$K_2CO_3$ solution (5 g of K2.2.2, 1 mg of $K_2CO_3$, MeCN (1.5 ml), water (0.5 ml)). The solvent was removed at 120° C. in a stream of nitrogen with addition of acetonitrile (three times 1 ml).

5 mg (14.9 µmol) of 1-tert-butyl 2-methyl 4-methanesulfonyloxy-5-oxopyrrolidine-1,2-dicarboxylate (8a) in 1 ml of acetonitrile were added and the resulting mixture was stirred for 10 min at 100° C. After cooling to about 60° C., the mixture was added by means of a Silica-Plus cartridge.

The intermediate was purified by HPLC (C18, acetonitrile/water). The HPLC fraction was diluted with water (about 50 ml) and added by means of a C18 cartridge. The intermediate was eluted using 1 ml of acetonitrile. 421 MBq (23% d.c.) of 1-tert-butyl 2-methyl 4-[F-18]fluoro-5-oxopyrrolidine-1,2-dicarboxylate were obtained in a synthesis time of 95 min.

Synthesis of 4[F-18]fluoroglutamic acid (5) by deprotection of 1-tert-butyl 2-methyl 4-[F-18]fluoro-5-oxopyrrolidine-1,2-dicarboxylate 221 MBq of 1-tert-butyl 2-methyl 4-[F-18]fluoro-5-oxopyrrolidine-1,2-dicarboxylate contained in 0.5 ml of acetonitrile were treated with 0.5 ml of 6N HCl. The mixture was heated at 130° C. (oil bath temperature) for 10 min with stirring. After cooling to room temperature, the solution was neutralized by addition of about 600 µl of 4N NaOH.

172 MBq (91% d.c.) of 4-[F-18]fluoroglutamic acid (5) were obtained.

Example 7

Synthesis of 1-tert-butyl 2-methyl 4-[2-(toluene-4-sulfonyloxy)ethoxy]pyrrolidine-1,2-dicarboxylate A solution of 2.45 g (10.0 mmol) of 1-tert-butyl 2-methyl 4-[hydroxy]pyrrolidine-1,2-dicarboxylate (24) in DMF (10 ml) was added to a suspension of 0.65 g (15 mmol) of sodium hydride in DMF (20 ml). After 15 min, a solution of 5.56 g (15.0 mmol) of 1,2-ethanediol bistosylate in DMF (10 ml) was added. The batch was subsequently reacted in 3 portions at 100° C. in a microwave for 45 minutes. The batch was concentrated and treated with water and ethyl acetate. After phase separation, the aqueous phase was extracted with ethyl acetate. The combined organic phases were dried over sodium sulfate, filtered and the solvent was removed in vacuo. The crude product was purified by column chromatography (silica gel, hexane/ethyl acetate). 1.2 g (27%) of 1-tert-butyl 2-methyl 4-[2-(toluene-4-sulfonyloxy)ethoxy]pyrrolidine-1,2-dicarboxylate were obtained.

Elemental analysis $C_{20}H_{29}NO_8S$. found C, 54.20; H, 6.66; N, 3.23; calculated: C, 54.16; H, 6.59; N, 3.16.

Synthesis of 1-tert-butyl 2-methyl 5-oxo-4-[2-(toluene-4-sulfonyloxy)ethoxy]-pyrrolidine-1,2-dicarboxylate (23)

A solution of 1.07 g (5.0 mmol) of sodium periodate and 0.338 g (0.15 mmol) of ruthenium(III) chloride hydrate in 12.5 ml of water was added to 0.44 g (1 mmol) of 1-tert-butyl 2-methyl 4-[2-(toluene-4-sulfonyloxy)ethoxy]pyrrolidine-1,2-dicarboxylate in 20 ml of dichloromethane. The mixture was left at room temperature for three days with vigorous stirring. Subsequently, the phases were separated, the aqueous phase was extracted twice with ethyl acetate (20 ml) and the combined organic phases were stirred with 5 ml of isopropanol for 30 min. The mixture was dried over magnesium sulfate, filtered and the solvent was removed in vacuo. The crude product was purified by column chromatography (silica gel, hexane/ethyl acetate). 0.11 g (24%) of 1-tert-butyl 2-methyl 5-oxo-4-[2-(toluene-4-sulfonyloxy)ethoxy]pyrrolidine-1,2-dicarboxylate (23) was obtained as a colorless oil.

Elemental analysis $C_{20}H_{27}NO_9S$. found C, 52.37; H, 6.02; N, 3.11; calculated: C, 52.51; H, 5.95; N, 3.06.

Synthesis of dimethyl 2-tert-butoxycarbonylamino-4-[2-(toluene-4-sulfonyloxy)-ethoxy]pentanedicarboxylate (25)

100 mg (0.22 mmol) of 1-tert-butyl 2-methyl 5-oxo-4-[2-(toluene-4-sulfonyloxy)ethoxy]-pyrrolidine-1,2-dicarboxylate were dissolved in 3 ml of dichloromethane. 1 ml of methanol and 6 mg (0.04 mmol) of potassium carbonate was added. The resulting mixture was stirred at room temperature for three hours. Subsequently, the solvent was removed in vacuo and the crude product was by column chromatography (silica gel, dichloromethane/methanol). mg (91%) of dimethyl 2-tert-butoxycarbonylamino-4-[2-(toluene-4-sulfonyloxy)ethoxy]pentanedicarboxylate (25) were obtained as a colorless oil.

Elemental analysis $C_{21}H_{31}NO_{10}S$. found C, 51.48; H, 6.36; N, 2.88; calculated: C, 51.52; H, 6.38; N, 2.86.

F-18 Labeling of dimethyl 2-tert-butoxycarbonylamino-4-[2-(toluene-4-sulfonyloxy)-ethoxy]pentanedicarboxylate (25)

[F-18]Fluoride was prepared in a cyclotron by means of the [O-18](p,n)[F-18] reaction. The isotope solution (1.57 GBq) was added to a Sep-Pack Light QMA-cartridge. The [F-18] fluoride was eluted from the cartridge using a Kryptofix 2.2.2/$K_2CO_3$ solution (5 g of K2.2.2, 1 mg of $K_2CO_3$, MeCN (1.5 ml), water (0.5 ml)). The solvent was removed at 120° C. in a stream of nitrogen with addition of acetonitrile (three times 1 ml).

5 mg (10.2 µmol) of dimethyl 2-tert-butoxycarbonylamino-4-[2-(toluene-4-sulfonyloxy)-ethoxy]pentanedicarboxylate (25) in 1 ml of acetonitrile were added and the resulting mixture was stirred at 100° C. for 10 min. After cooling to about 60° C., the mixture was added by means of a Silica-Plus cartridge.

The intermediate was purified by HPLC (C18, acetonitrile/water). The HPLC fraction was diluted with water (about 50 ml) and added by means of a C18 cartridge. The intermediate was eluted with 1 ml of acetonitrile. In a synthesis time of 78 min, 337 MBq (35% d.c.) of dimethyl 2-tert-butoxycarbonylamino-4-(2-[F-18]fluoroethoxy)pentanedicarboxylate were obtained (22).

Synthesis of 2-amino-4-(2[F-18]fluoroethoxy)pentanedicarboxylic acid (20) by deprotection of dimethyl 2-tert-butoxycarbonylamino-4-(2-[F-18]fluoroethoxy)-pentanedicarboxylate (22)

337 MBq of dimethyl 2-tert-butoxycarbonylamino-4-(2-[F-18]fluoroethoxy)pentanedi-carboxylate (22) in 1 ml of acetonitrile were treated with 0.5 ml of 4N HCl. The mixture was heated for 10 min with stirring at 130° C. (oil bath temperature). After cooling to room temperature, the solution was neutralized by addition of about 700 µl of 2N NaOH.

288 MBq (98% d.c.) of 2-amino-4-(2-[F-18]fluoroethoxy)pentanedicarboxylic acid (20) were obtained.

Synthesis of 1-tert-butyl 2-methyl 4-(2-fluoroethoxy)pyrrolidine-1,2-dicarboxylate A solution of 2.45 g (10.0 mmol) of 1-tert-butyl 2-methyl 4-[hydroxy]pyrrolidine-1,2-dicarboxylate (24) in DMF (10 ml) was added to a suspension of 0.65 g (15 mmol) of sodium hydride in DMF (20 ml). After 15 min, a solution of 1.90 g (15.0 mmol) of 1-bromo-2-fluoroethane in DMF (10 ml) was added. The batch was subsequently reacted in 3 portions at 100° C. in a microwave for 45 minutes. The batch was concentrated and treated with water and ethyl acetate. After phase separation, the aqueous phase was extracted with ethyl acetate. The combined organic phases were dried over sodium sulfate, filtered and the solvent was removed in vacuo. The crude product was purified by column chromatography (silica gel, hexane/ethyl acetate). 2.10 g (48%) of 1-tert-butyl 2-methyl 4-(2-fluoroethoxy)-pyrrolidine-1,2-dicarboxylate were obtained.

Elemental analysis $C_{13}H_{22}FNO_5$. found C, 53.48; H, 7.70; N, 4.85; calculated: C, 53.60; H, 7.61; N, 4.81.

1-tert-Butyl 2-methyl 4-(2-fluoroethoxy)-5-oxopyrrolidine-1,2-dicarboxylate (26)

A solution of 4.3 g (20.0 mmol) of sodium periodate and 1.7 g (0.6 mmol) of ruthenium(III) chloride hydrate in 50 ml of water was added to 1.45 g (5 mmol) of 1-tert-butyl 2-methyl 4-(2-fluoroethoxy)pyrrolidine-1,2-dicarboxylate in 80 ml of dichloromethane. The mixture was left at room temperature for three days with vigorous stirring. Subsequently, the phases were separated, the aqueous phase was extracted twice with ethyl acetate (25 ml) and the combined organic phases were stirred with 10 ml of isopropanol for 30 min. The mixture was dried over sodium sulfate, filtered and the solvent was removed in vacuo. The crude product was purified by column chromatography (silica gel, hexane/ethyl acetate). 0.26 g (17%) of 1-tert-butyl 2-methyl 4-(2-fluoroethoxy)-5-oxopyrrolidine-1,2-dicarboxylate (26) was obtained as.

Elemental analysis $C_{13}H_{20}FNO_6$. found C, 51.18; H, 6.55; N, 3.54; calculated: C, 51.14; H, 6.60; N, 4.59.

Dimethyl 2-tert-butoxycarbonylamino-4-(2-fluoroethoxy)pentanedicarboxylate (27)

150 mg (0.49 mmol) of 1-tert-butyl 2-methyl 4-(2-fluoroethoxy)-5-oxopyrrolidine-1,2-dicarboxylate (26) were dissolved in 5 ml of dichloromethane. 2 ml of methanol and 6 mg (0.04 mmol) of potassium carbonate were added. The resulting mixture was stirred at room temperature for three hours. Subsequently, the solvent was removed in vacuo and the crude product was by column chromatography (silica gel, dichloromethane/methanol). 145 mg (88%) of dimethyl 2-tert-butoxycarbonylamino-4-(2-fluoroethoxy)pentanedicarboxylate (27) were obtained.

Elemental analysis $C_{14}H_{24}FNO_7$. found C, 40.06; H, 7.11; N, 4.12; calculated: C, 49.85; H, 7.17; N, 4.15

2-Amino-4-(2-fluoroethoxy)pentanedicarboxylic acid (28)

100 mg of dimethyl 3-tert-butoxycarbonylamino-4-(2-fluoroethoxy)pentanedicarboxylate (27) were dissolved in 50 ml of MeOH and treated with stirring with 1 ml of HCl (6N). The reaction mixture was heated to reflux for 15-20 min, concentrated to dryness, diluted with 50 ml of water, and the hydrochloride was filtered off and carefully washed with 3×5 ml of water. The amino acid 28 was isolated by means of ion exchange chromatography on a 50 w×8 Dowex column in H$^+$ form (eluent: 5% NH$_3$ aq).

Example 8

Synthesis of di methyl 2-(3-bromopropyl)-4-tert-butoxycarbonylaminopentane-dicarboxylate (33)

(according to: S. Hanessian, et al. *J. Org. Chem.* 2005, 70, 5070-5085.) LiHMDS (7.8 ml, 1M solution in THF) was added at −78° C. to a solution of 1.00 g (3.63 mmol) of dimethyl N-Boc-glutamate (26) in dry THF (20 ml). The resulting mixture was stirred for 45 min at −78° C. Subsequently, a solution of 1.10 g (5.45 mmol) of 1,3-dibromopropane in THF (10 ml) was slowly added dropwise at −78° C. The mixture was stirred for 60 min. It was quenched by addition of ammonium chloride solution, warmed to RT and extracted with dichloromethane. The combined organic phases were washed with saturated sodium chloride solution and dried over sodium sulfate. The solvent was removed in vacuo and the crude product was purified by column chromatography (silica gel, ethyl acetate/hexane 10:90 to 40:60). 0.490 g (34%) of dimethyl 2-(3-bromopropyl)-4-tert-butoxycarbonylaminopentanedicarboxylate (33) were obtained as a colorless oil.

Elemental analysis C15H26BrNO6. found C, 45.21; H, 6.53; N, 3.60; calculated: C, 45.46; H, 6.61; N, 3.53.

F-18 Labeling of dimethyl 2-(3-bromopropyl)-4-tert-butoxycarbonylaminopentane-dicarboxylate (33)

[F-18]Fluoride was prepared in a cyclotron by means of the [O-18](p,n)[F-18] reaction. The isotope solution (1.33 GBq) was added to a Sep-Pack Light QMA cartridge. The [F-18]fluoride was eluted from the cartridge using a Kryptofix 2.2.2/K$_2$CO$_3$ solution (5 g of K2.2.2, 1 mg of K$_2$CO$_3$, MeCN (1.5 ml), water (0.5 ml)). The solvent was removed at 120° C. in a stream of nitrogen with addition of acetonitrile (three times 1 ml).

5 mg (12.6 µmol) of dimethyl 2-(3-bromopropyl)-4-tert-butoxycarbonylaminopentane-dicarboxylate (33) in 1 ml of acetonitrile were added and the resulting mixture was stirred for 10 min at 100° C. After cooling to about 60° C., the mixture was added by means of a Silica-Plus cartridge.

The intermediate was purified by HPLC (C18, acetonitrile/water). The HPLC fraction was diluted with water (about 50 ml) and added by means of a C18 cartridge. The intermediate was eluted using 1 ml of acetonitrile. In a synthesis time of 90 min, 346 MBq (46% d.c.) of dimethyl 2-tert-butoxycarbonylamino-4-(3-[F-18]fluoropropyl)pentanedicarboxylate (31) were obtained.

Synthesis of 2-amino-4-(3[F-18]fluoropropyl)pentanedicarboxylic acid (29) by deprotection of dimethyl 2-tert-butoxycarbonylamino-4-(3-[F-18]fluoropropyl)-pentanedicarboxylate (31)

346 MBq of dimethyl 2-tert-butoxycarbonylamino-4-(3-[F-18]fluoropropyl)pentane-dicarboxylate (3) in 1 ml of acetonitrile were treated with 0.5 ml of 4N HCl. The mixture was heated with stirring at 130° C. (oil bath temperature) for 10 min. After cooling to room temperature, the solution was neutralized by addition of about 650 µl of 2N NaOH.

288 MBq (96% d.c.) of 2-amino-4-(3-[F-18]fluoropropyl) pentanedicarboxylic acid (29) were obtained.

Synthesis of dimethyl 2-tert-butoxycarbonylamino-4-(3-fluoropropyl)pentane-dicarboxylate (36)

(according to: S. Hanessian, et al. *J. Org. Chem.* 2005, 70, 5070-5085.) LiHMDS (7.8 ml, 1M solution in THF) was added at −78° C. to a solution of 1.00 g (3.63 mmol) of dimethyl N-Boc-glutamate (26) in dry THF (20 ml). The resulting mixture was stirred for 45 min at −78° C. Subsequently, a solution of 0.77 g (5.45 mmol) of 1-bromo-3-fluoropropane in THF (10 ml) was slowly added dropwise at −78° C. The mixture was stirred for 60 min. It was quenched by addition of ammonium chloride solution, warmed to RT and extracted with dichloromethane. The combined organic phases were washed with saturated sodium chloride solution and dried over sodium sulfate. The solvent was removed in vacuo and the crude product was purified by column chromatography (silica gel, ethyl acetate/hexane 10:90 to 40:60). 0.318 g (29%) of dimethyl 2-tert-butoxycarbonylamino-4-(3-fluoropropyl)pentanedicarboxylate (36) was obtained.

Elemental analysis $C_{15}H_{26}FNO_6$. found C, 53.88; H, 7.87; N, 4.13; calculated: C, 53.72; H, 7.81; N, 4.18.

2-Amino-4-(2-fluoropropyl)pentanedicarboxylic acid (38)

200 mg of dimethyl 2-tert-butoxycarbonylamino-4-(3-fluoropropyl)pentanedicarboxylate (36) were dissolved in 75 ml of MeOH and treated with 1.5 ml of HCl (6N) with stirring. The reaction mixture was heated to reflux for 15-20 min, concentrated to dryness, diluted with 50 ml of water, and the hydrochloride was filtered off and carefully washed with 3×10 ml of water. The amino acid 38 was isolated in H$^+$ form by means of ion exchange chromatography on a 50 w×8 Dowex column (eluent: 5% $NH_3$ aq).

Example 9

Synthesis of dimethyl 2-tert-butoxycarbonylamino-4-[4-(toluene-4-sulfonyloxy)butyl]-pentanedicarboxylate (34)

(according to: S. Hanessian, et al. *J. Org. Chem.* 2005, 70, 5070-5085.)
LiHMDS (7.8 ml, 1M solution in THF) was added at −78° C. to a solution of 1.00 g (3.63 mmol) of dimethyl N-Boc-glutamate (35) in dry THF (20 ml). The resulting mixture was stirred at −78° C. for 45 min. Subsequently, a solution of 2.17 g (5.45 mmol) of 1,4-butanediol ditosylate in THF (10 ml) was slowly added dropwise at −78° C. The mixture was stirred for 60 min. It was quenched by addition of ammonium chloride solution, warmed to RT and extracted with dichloromethane. The combined organic phases were washed with saturated sodium chloride solution and dried over sodium sulfate. The solvent was removed in vacuo and the crude product was purified by column chromatography (silica gel, ethyl acetate/hexane 10:90 to 20:80). 0.418 g (23%) of dimethyl 2-tert-butoxycarbonylamino-4-[4-(toluene-4-sulfonyloxy)butyl]pentanedicarboxylate (34) was obtained.

Elemental analysis $C_{23}H_{35}NO_9S$. found C, 54.9; H, 7.1; N, 2.7; calculated: C, 55.07; H, 7.03; N: 2.79.

F-18 Labeling of dimethyl 2-tert-butoxycarbonylamino-4-[4-(toluene-4-sulfonyloxy)-butyl]pentanedicarboxylate (34)

[F-18]Fluoride was prepared in a cyclotron by means of the [O-18](p,n)[F-18] reaction. The isotope solution (3.08 GBq) was added to a Sep-Pack Light QMA cartridge. The [F-18]fluoride was eluted from the cartridge using a Kryptofix 2.2.2/$K_2CO_3$ solution (5 g of K2.2.2, 1 mg of $K_2CO_3$, MeCN (1.5 ml), water (0.5 ml)). The solvent was removed at 120° C. in a stream of nitrogen with addition of acetonitrile (three times 1 ml).
5 mg (10.0 µmol) of dimethyl 2-tert-butoxycarbonylamino-4-[4-(toluene-4-sulfonyloxy)butyl]-pentanedicarboxylate (34) in 1 ml of acetonitrile were added and the resulting mixture was stirred at 100° C. for 10 min. After cooling to about 60° C., the mixture was added by means of a Silica-Plus cartridge.

The intermediate was purified by HPLC (C18, acetonitrile/water). The HPLC fraction was diluted with water (about 50 ml) and added by means of a C18 cartridge. The intermediate was eluted using 1 ml of acetonitrile. In a synthesis time of 92 min, 812 MBq (48% d.c.) of dimethyl 2-tert-butoxycarbonylamino-4-(4-[F-18]fluorobutyl)pentanedicarboxylate (32) were obtained.

Synthesis of dimethyl 2-amino-4-(4-fluorobutyl)pentanedicarboxylic acid (30) by deprotection of 2-tert-butoxycarbonylamino-4-(4-[F-18]fluorobutyl)pentane-dicarboxylate (32)

812 MBq of dimethyl 2-tert-butoxycarbonylamino-4-(4-[F-18]fluorobutyl)pentane-dicarboxylate (32) in 1 ml of acetonitrile were treated with 0.5 ml of 4N HCl. The mixture was heated with stirring to 130° C. (oil bath temperature) for 10 min. After cooling to room temperature, the solution was neutralized by addition of about 700 µl of 2N NaOH. 691 MBq (97% d.c.) of 2-amino-4-(4-fluorobutyl)pentanedicarboxylic acid (30) were.

Synthesis of di methyl 2-tert-butoxycarbonylamino-4-(3-fluorobutyl)pentane-dicarboxylate (37)

(according to: S. Hanessian, et al. *J. Org. Chem.* 2005, 70, 5070-5085.) LiHMDS (7.8 ml, 1M solution in THF) was added at −78° C. to a solution of 1.00 g (3.63 mmol) of dimethyl N-Boc-glutamate (26) in dry THF (20 ml). The resulting mixture was stirred for 45 min at −78° C. Subsequently, a solution of 0.84 g (5.45 mmol) of 1-bromo-3-fluoropropane in THF (10 ml) was slowly added dropwise at −78° C. The mixture was stirred for 60 min. It was quenched by addition of ammonium chloride solution, warmed to RT and extracted with dichloromethane. The combined organic phases were washed with saturated sodium chloride solution and dried over sodium sulfate. The solvent was removed in vacuo and the crude product was purified by column chromatography (silica gel, ethyl acetate/hexane 10:90 to 40:60). 0.596 g (47%) of dimethyl 2-tert-butoxycarbonylamino-4-(3-fluorobutyl)-pentanedicarboxylate (37) was obtained.

Elemental analysis $C_{16}H_{28}FNO_6$. found C, 54.94; H, 8.01; N, 4.04; calculated: C, 55.00; H, 8.08; N, 4.01.

2-Amino-4-(2-fluoropropyl)pentanedicarboxylic acid (39)

300 mg of dimethyl 2-tert-butoxycarbonylamino-4-(3-fluorobutyl)pentanedicarboxylate (37) were dissolved in 100 ml of MeOH and treated with 5 ml of HCl (6N) with stirring. The reaction mixture was heated to reflux for 15-20 min, concentrated to dryness, diluted with 100 ml of water, and the hydrochloride was filtered off and carefully washed with 3×25 ml of water. The amino acid 38 was isolated by means of ion exchange chromatography on a 50 w×8 Dowex column in H$^+$ form (eluent: 5% $NH_3$ aq).

Example 10

Biological Characterization

For the evaluation of the tumor cell uptake of [$^{18}$F]glutamic acid, cell uptake experiments were carried out in human A549

(non-small-cell bronchial carcinoma) and HT29 (colonic carcinoma) cells. The tumor cell uptake of the glutamic acid derivatives was compared to

[$^{18}$F]FDG (gold standard for oncological PET investigations).

The results are shown in FIG. 1.

FIG. 2: Comparison of the time-dependent tumor cell uptake of [$^{18}$F]-4-glutamic acid [20-35 µM] (on the left) and [F-18]FDG [2 µM] (on the right) in A549 cells. The cells were incubated with 250 kBq/well. For displacement experiments, L-glutamic acid (1 mM) or glucose (5 mM) was used (mean value±standard deviation, n=3).

The surprisingly high uptake of [$^{18}$F]-4-glutamic acid in A549 and HT29 tumor cells shows that these fluorinated glutamic acid derivatives should have potential for tumor demonstration for the purposes of the invention.

Analogous uptake results were achieved for [$^{18}$F]-4-glutamine, 2-amino-4-(2-[F-18]fluoro-ethoxy)pentanedicarboxylic acid and 2-amino-4-(3-[F-18]fluoropropyl)pentanedicarboxylic acid.

For the evaluation of the tumor enrichment and the tissue distribution in experimental animals, [$^{18}$F]-4-glutamic acid was tested in a murine F9 teratocarcinoma model in NMRI nude mice and a murine B16F1 melanoma model in C57BI6 mice.

For this, 1×10$^6$ cells (F9) or 5×10$^5$ cells (B16F1) respectively were suspended in 100 µl of phosphate-buffered physiological saline solution and inoculated subcutaneously into the right, rear flank of the corresponding experimental animal species (NMRI for F9 and 057-BI6 for B16F1) (Berndorff et al. Clin. Cancer Res. 2005, 11, 2005). After 14 days (F9) and 10 days (B16), the tumors achieved a size of about 80-100 mm$^2$. [$^{18}$F]-4-Glutamic acid (370 kBq, in 100 µl of physiological saline solution) was administered intravenously to the tail vein. After 15; 60 and 120 min in each case, the animals were killed, organ and tumor removed, weighed and measured for radioactive content. The corresponding data are summarized in tables 1-4.

The tissue distributions of [$^{18}$F]-4-glutamic acid were compared in the same tumor models with those of C-14 labeled glutamic acid, where 111 kBq of [$^{14}$C]5-glutamic acid was administered intravenously and the animals were killed and analyzed after 30, 60 and 240 min (F9) and after 15, 60 and 120 min (B16F1) (tables 5-8).

In comparison to these results, C-14-labeled glutamic acid was investigated in both tumor models. The corresponding organ distribution results are reproduced in tab. 5-9.

Surprisingly, [$^{18}$F]4-glutamic acid after intravenous injection (15 min) shows a maximal tumor enrichment of 2.90% ID/g (F9 teratocarcinoma) or 3.55% ID/g (B16 melanoma) whereas the maximal tumor enrichment at the similarly early time (30 min) for the natural substrate [$^{14}$C]5-glutamic acid is only 0.81% ID/g in the F9 teratocarcinoma and at the same time 1.23 in the B16F1 melanoma.

Even 1 h after intravenous administration, the values are distinctly higher with 1.75% ID/g in the F9 teratocarcinoma and 2.14% ID/g in the B16F1 melanoma than for [$^{14}$C]5-glutamic acid with only 0.98% ID/g (F9 teratocarcinoma) and 1.03% ID/g (B16F1 melanoma).

The higher tumor enrichment of the fluorinated compound linked with a rapid excretion from physiological, vital tissue/organs leads to a distinctly improved tumor/background ratio of [$^{18}$F]4 glutamic acid relative to [$^{14}$C]5-glutamic acid. The tumor/blood quotient in the B16F1 melanoma model for the fluorinated compound is 5.3 (1 h p.i.) and 7.9 (2 h p.i), and is thus higher by the factor 2 and 3.5 respectively than for [$^{14}$C]5-glutamic acid.

The tumor/liver quotient, an important parameter for the suitability assessment of a PET tracer, for the fluorinated compound in the B16F1 melanoma model is 3.6 (1 h p.i.) and 4.4 (2 h p.i), and is thus higher by the factor 4.6 and 5.5 respectively than for [$^{14}$C]5-glutamic acid.

[$^{18}$F]4-Glutamic acid has distinctly improved pharmacokinetic properties compared with the C-14-substituted natural substrate [$^{14}$C]5-glutamic acid.

TABLE 1

Figure 1:
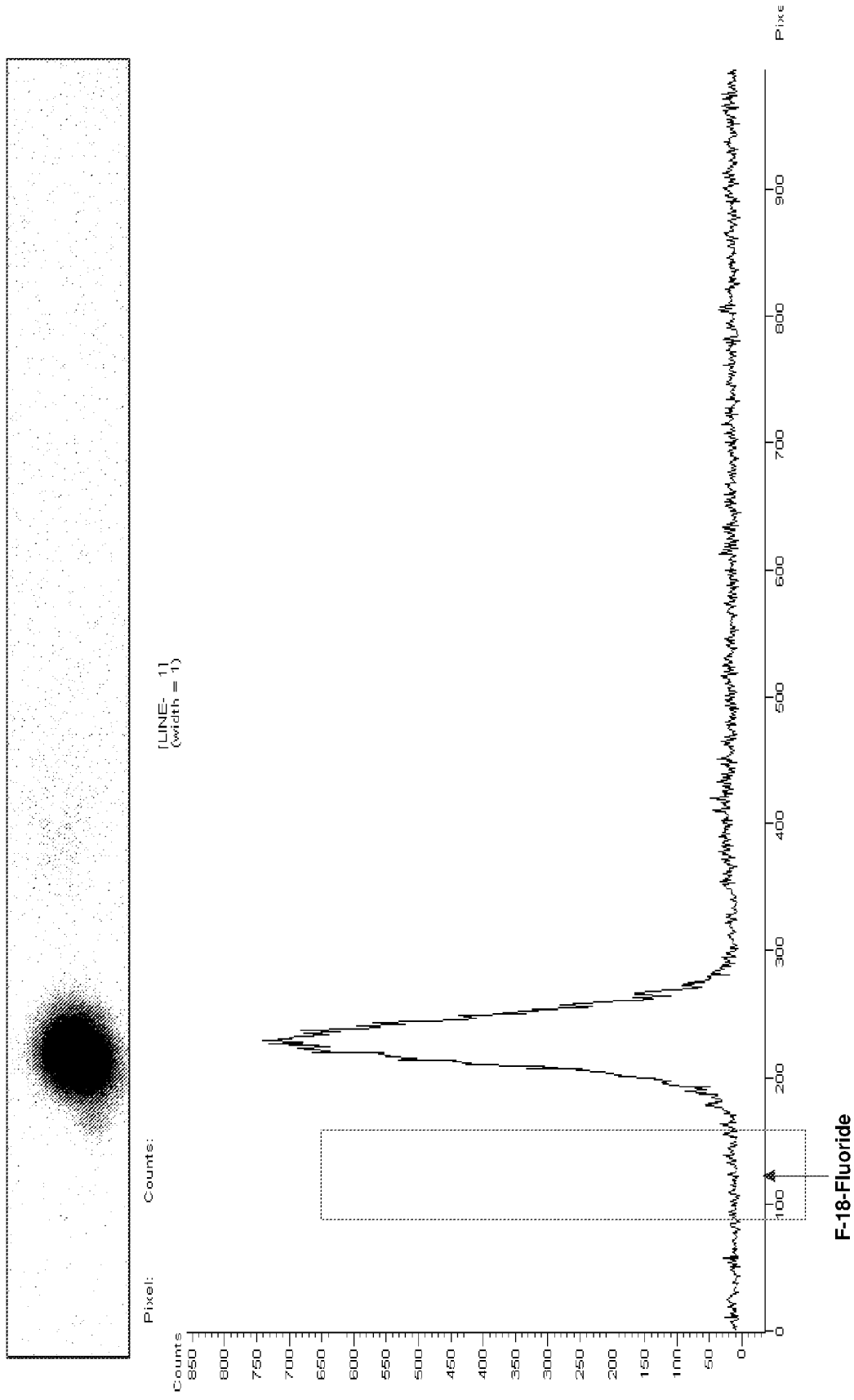
In FIG. 1, identification of 4-[F-18]-Glu is shown with radio-TLC, and the tumor enrichment and the uptake for 4-[F-18]F-Glu is shown in selected relevant organs after 1 h (a) and 2 h (b) respectively.
Figure 2:
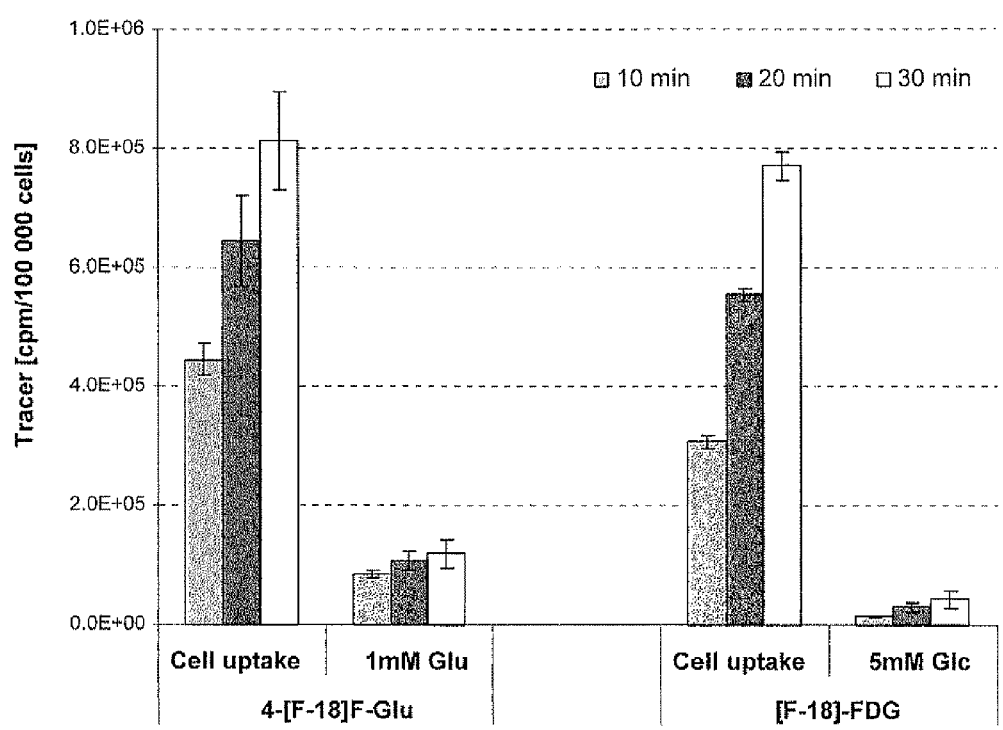
FIG. 2 shows a companion of the time-dependent tumor-cell uptake of 4[F-18]F-Glu and [F-18]FDG.
Figure 3:
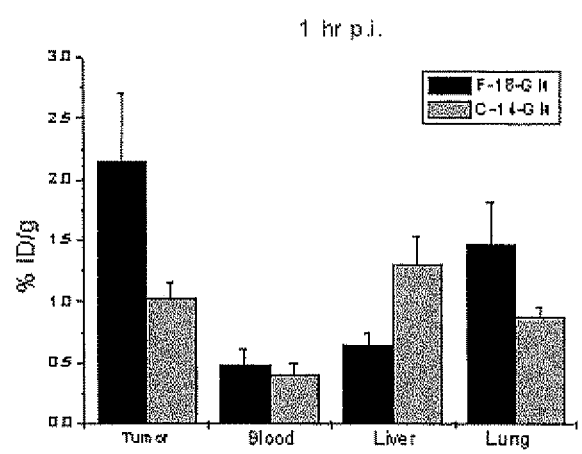
FIG. 3 shows the distribution after 1 h.
Figure 4:
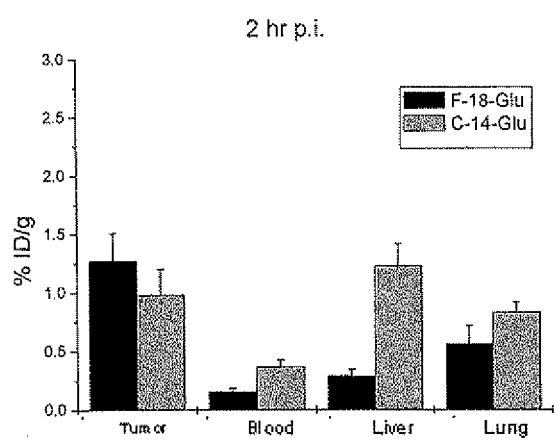
In FIG. 4, the distribution after 2 h is shown.
Figure 5:
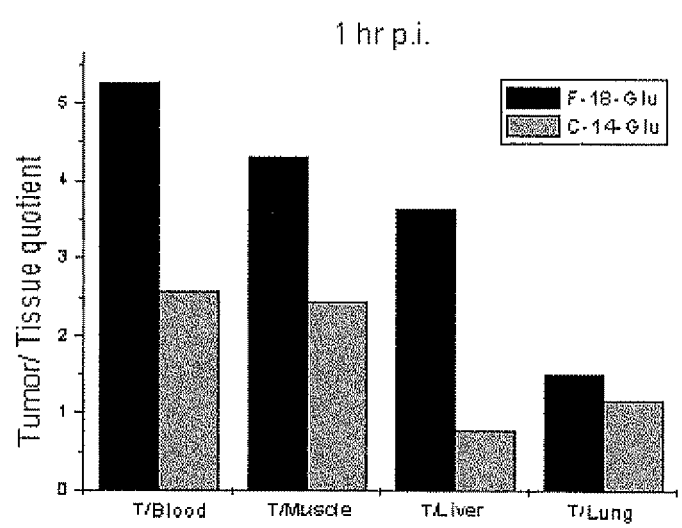
FIG. 5 shows the resulting tissue quotients including tumor/muscle tissue after 1 h.
Figure 6:
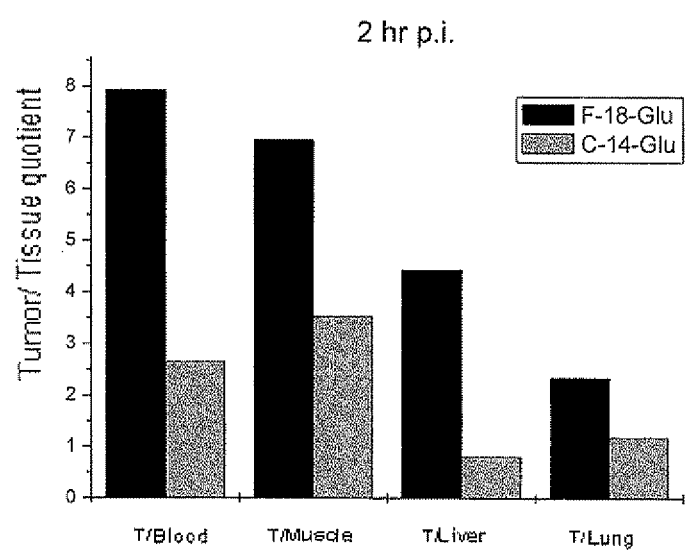
FIG. 6 shows the resulting tissue quotients including tumor/muscle tissue after 2 h.

Tissue uptake (% injected dose per g of tissue) of [$^{18}$F]4-glutamic acid in the murine, embryonic teratocarcinoma F9 in NMRI nude mice after single intravenous administration.

| | Time: | | | | | |
|---|---|---|---|---|---|---|
| | 0.25 h | | 1.0 h | | 2.0 h | |
| % dose/g | | S.D. | | S.D. | | S.D. |
| Spleen | 2.56 | 0.64 | 0.54 | 0.04 | 0.16 | 0.09 |
| Liver | 3.37 | 0.84 | 0.50 | 0.02 | 0.20 | 0.03 |
| Kidney | 7.24 | 1.33 | 1.30 | 0.17 | 0.37 | 0.12 |
| Lung | 5.08 | 1.19 | 1.32 | 0.24 | 0.48 | 0.10 |
| Heart | 2.86 | 0.67 | 0.64 | 0.08 | 0.21 | 0.04 |
| Brain | 0.52 | 0.15 | 0.43 | 0.11 | 0.27 | 0.03 |
| Fat | 0.85 | 0.83 | 0.26 | 0.08 | 0.09 | 0.03 |
| Muscle | 1.72 | 0.10 | 0.70 | 0.03 | 0.42 | 0.50 |
| Tumor | 2.90 | 0.86 | 1.75 | 0.21 | 1.87 | 0.38 |
| Skin | 2.28 | 0.38 | 0.53 | 0.09 | 0.21 | 0.09 |
| Blood | 2.51 | 0.43 | 0.51 | 0.04 | 0.21 | 0.08 |
| Stomach | 2.56 | 0.62 | 1.26 | 1.29 | 0.33 | 0.16 |
| Ovary | 1.34 | 0.45 | 0.41 | 0.16 | 0.12 | 0.05 |
| Uterus | 2.54 | 0.48 | 0.72 | 0.19 | 0.32 | 0.18 |
| Intestine | 2.28 | 0.31 | 1.83 | 0.24 | 1.21 | 0.16 |

TABLE 2

Tumor/tissue quotient of [$^{18}$F]4-glutamic acid in the murine, embryonic teratocarcinoma F9 in NMRI nude mice after single intravenous administration.

| Tu/Ti qu. | | S.D. | | S.D. | | S.D. |
|---|---|---|---|---|---|---|
| Spleen | 1.12 | 0.13 | 3.22 | 0.16 | 18 | 17.77 |
| Liver | 0.86 | 0.18 | 3.48 | 0.29 | 9.23 | 1.32 |
| Kidney | 0.4 | 0.07 | 1.38 | 0.35 | 5.22 | 0.53 |
| Lung | 0.57 | 0.04 | 1.34 | 0.15 | 4.09 | 1.41 |
| Heart | 1.01 | 0.15 | 2.73 | 0.24 | 9.22 | 1.9 |
| Brain | 5.6 | 0.93 | 4.2 | 0.59 | 7.06 | 1.96 |
| Fat | 5.85 | 5 | 7.37 | 2.87 | 23.67 | 9.1 |
| Muscle | 1.67 | 0.42 | 2.51 | 0.32 | 9.5 | 6.61 |
| Skin | 1.25 | 0.23 | 3.4 | 0.95 | 9.4 | 1.74 |
| Blood | 1.14 | 0.18 | 3.46 | 0.36 | 9.06 | 1.19 |
| Stomach | 1.12 | 0.09 | 2.45 | 1.56 | 6.85 | 3.86 |

TABLE 2-continued

Tumor/tissue quotient of [$^{18}$F]4-glutamic acid in the murine, embryonic teratocarcinoma F9 in NMRI nude mice after single intravenous administration.

| Tu/Ti qu. | | S.D. | | S.D. | | S.D. |
|---|---|---|---|---|---|---|
| Intestine | 1.26 | 0.27 | 0.97 | 0.18 | 1.54 | 0.11 |
| Ovary | 2.43 | 1.22 | 5.05 | 2.93 | 17.74 | 7.63 |
| Uterus | 1.18 | 0.46 | 2.59 | 0.92 | 6.96 | 3.18 |

TABLE 3

Tissue uptake (% injected dose per g of tissue) of [$^{18}$F]4-glutamic acid in the murine, syngeneic, B16 melanoma in C57Bl6 mice after single intravenous administration.

| | Time: | | | | | |
|---|---|---|---|---|---|---|
| | 0.25 h | | 1.0 h | | 2.0 h | |
| % dose/g | | S.D. | | S.D. | | S.D. |
| Spleen | 4.07 | 0.54 | 0.81 | 0.12 | 0.31 | 0.04 |
| Liver | 3.81 | 0.06 | 0.64 | 0.10 | 0.29 | 0.06 |
| Kidney | 11.35 | 0.66 | 2.25 | 0.97 | 0.57 | 0.13 |
| Lung | 11.10 | 0.60 | 1.47 | 0.34 | 0.56 | 0.16 |
| Heart | 3.36 | 0.09 | 0.71 | 0.20 | 0.28 | 0.10 |
| Brain | 0.73 | 0.03 | 0.49 | 0.16 | 0.36 | 0.08 |
| Fat | 0.92 | 0.16 | 0.18 | 0.05 | 0.16 | 0.06 |
| Muscle | 2.19 | 0.75 | 0.53 | 0.13 | 0.24 | 0.16 |
| Tumor | 3.55 | 0.17 | 2.14 | 0.57 | 1.27 | 0.24 |
| Skin | 2.43 | 0.36 | 0.48 | 0.14 | 0.22 | 0.06 |
| Blood | 2.93 | 0.15 | 0.48 | 0.13 | 0.16 | 0.03 |
| Stomach | 3.41 | 0.28 | 0.59 | 0.20 | 0.30 | 0.05 |
| Ovary | 3.57 | 0.79 | 0.58 | 0.17 | 0.45 | 0.19 |
| Uterus | 7.17 | 3.27 | 0.69 | 0.20 | 0.76 | 0.56 |
| Intestine | 3.00 | 0.32 | 1.28 | 0.25 | 1.46 | 0.09 |

TABLE 4

Tumor/tissue quotient of [$^{18}$F]4-glutamic acid in the murine, syngeneic, B16 melanoma in C57Bl6 mice after single intravenous administration.

| Tu/Ti qu. | | S.D. | | S.D. | | S.D. |
|---|---|---|---|---|---|---|
| Spleen | 0.89 | 0.14 | 2.81 | 0.30 | 4.03 | 0.39 |
| Liver | 0.93 | 0.05 | 3.63 | 0.57 | 4.42 | 0.31 |
| Kidney | 0.31 | 0.03 | 1.25 | 0.13 | 2.22 | 0.22 |
| Lung | 0.32 | 0.01 | 1.51 | 0.1 | 2.34 | 0.49 |
| Heart | 1.06 | 0.08 | 3.54 | 0.53 | 5.06 | 2.1 |
| Brain | 4.89 | 0.34 | 4.7 | 1.04 | 3.55 | 0.34 |
| Fat | 3.95 | 0.81 | 14.16 | 1.1 | 8.85 | 3.19 |
| Muscle | 1.72 | 0.44 | 4.3 | 2.47 | 6.95 | 3.5 |
| Skin | 1.49 | 0.25 | 5.43 | 1.53 | 5.94 | 0.54 |
| Blood | 1.21 | 0.12 | 5.25 | 1.12 | 7.93 | 0.96 |
| Stomach | 1.05 | 0.12 | 4.02 | 0.96 | 4.24 | 0.63 |
| Intestine | 1.19 | 0.15 | 1.56 | 0.08 | 0.87 | 0.13 |
| Ovary | 1.03 | 0.27 | 4.38 | 0.85 | 3.02 | 0.79 |
| Uterus | 0.56 | 0.23 | 3.84 | 1.76 | 2.59 | 2.06 |

TABLE 5

Tissue uptake (% injected dose per g of tissue) of [$^{14}$C]5-glutamic acid in the murine, embryonic teratocarcinoma F9 in NMRI nude mice after single intravenous administration.

| | Time: | | | | | |
|---|---|---|---|---|---|---|
| | 0.5 h | | 1.0 h | | 4.0 h | |
| % dose/g | | S.D. | | S.D. | | S.D. |
| Spleen | 0.78 | 0.12 | 0.55 | 0.06 | 0.52 | 0.03 |
| Liver | 1.10 | 0.37 | 0.75 | 0.10 | 0.59 | 0.10 |
| Kidney | 0.95 | 0.05 | 0.56 | 0.03 | 0.36 | 0.04 |
| Lung | 1.51 | 0.11 | 0.83 | 0.09 | 0.59 | 0.04 |
| Heart | 0.87 | 0.08 | 0.49 | 0.09 | 0.18 | 0.01 |
| Brain | 0.11 | 0.01 | 0.08 | 0.01 | 0.05 | 0.01 |
| Fat | 0.08 | 0.02 | 0.04 | 0.01 | 0.06 | 0.04 |
| Muscle | 0.40 | 0.14 | 0.29 | 0.05 | 0.19 | 0.05 |
| Tumor | 0.81 | 0.32 | 0.98 | 0.34 | 0.64 | 0.08 |
| Skin | 0.77 | 0.24 | 0.55 | 0.08 | 0.41 | 0.13 |
| Blood | 0.31 | 0.03 | 0.28 | 0.02 | 0.19 | 0.04 |
| Stomach | 1.54 | 0.31 | 1.16 | 0.33 | 0.80 | 0.16 |
| Ovary | 0.93 | 0.18 | 0.72 | 0.24 | 0.46 | 0.10 |
| Uterus | 0.75 | 0.25 | 0.51 | 0.14 | 0.43 | 0.19 |
| Intestine | 0.81 | 0.32 | 0.93 | 0.31 | 0.68 | 0.14 |

TABLE 6

Tumor/tissue quotient of [$^{14}$C]5-glutamic acid in the murine, embryonic teratocarcinoma F9 in NMRI nude mice after single intravenous administration.

| Tu/Ti qu. | | | |
|---|---|---|---|
| Spleen | 1.08 | 1.76 | 1.23 |
| Liver | 0.74 | 1.31 | 1.09 |
| Kidney | 0.85 | 1.74 | 1.81 |
| Lung | 0.53 | 1.17 | 1.10 |
| Heart | 0.92 | 1.99 | 3.53 |
| Brain | 7.12 | 12.39 | 13.64 |
| Fat | 10.13 | 24.01 | 10.02 |
| Muscle | 2.00 | 3.33 | 3.36 |
| Skin | 1.04 | 1.77 | 1.58 |
| Blood | 2.59 | 3.53 | 3.45 |
| Stomach | 0.52 | 0.84 | 0.80 |
| Intestine | 0.99 | 1.05 | 0.94 |
| Ovary | 0.86 | 1.35 | 1.40 |
| Uterus | 1.08 | 1.93 | 1.50 |

TABLE 7

Tissue uptake (% injected dose per g of tissue) of [$^{14}$C]5-glutamic acid in the murine, syngeneic, B16 melanoma in C57Bl6 mice after single intravenous administration.

| | Time: | | | | | |
|---|---|---|---|---|---|---|
| | 0.25 h | | 1.0 h | | 2.0 h | |
| % dose/g | | S.D. | | S.D. | | S.D. |
| Spleen | 1.91 | 0.33 | 1.16 | 0.39 | 0.72 | 0.15 |
| Liver | 2.34 | 0.40 | 1.30 | 0.23 | 1.23 | 0.19 |
| Kidney | 2.97 | 0.54 | 0.99 | 0.16 | 0.92 | 0.04 |
| Lung | 3.74 | 0.99 | 0.87 | 0.09 | 0.83 | 0.09 |
| Heart | 3.03 | 0.43 | 0.93 | 0.06 | 0.52 | 0.08 |
| Brain | 0.22 | 0.06 | 0.13 | 0.08 | 0.09 | 0.01 |
| Fat | 0.69 | 0.29 | 0.19 | 0.09 | 0.15 | 0.10 |
| Muscle | 1.15 | 0.19 | 0.42 | 0.06 | 0.28 | 0.07 |
| Tumor | 1.23 | 0.14 | 1.03 | 0.13 | 0.98 | 0.22 |
| Skin | 0.86 | 0.16 | 0.32 | 0.15 | 0.28 | 0.19 |
| Blood | 0.56 | 0.06 | 0.40 | 0.10 | 0.37 | 0.06 |
| Stomach | 2.71 | 1.54 | 2.11 | 0.77 | 1.60 | 0.57 |

TABLE 7-continued

Tissue uptake (% injected dose per g of tissue) of [$^{14}$C]5-glutamic acid in the murine, syngeneic, B16 melanoma in C57Bl6 mice after single intravenous administration.

| % dose/g | Time: | | | | | |
|---|---|---|---|---|---|---|
| | 0.25 h | S.D. | 1.0 h | S.D. | 2.0 h | S.D. |
| Ovary | 2.61 | 0.74 | 1.01 | 0.48 | 1.18 | 0.03 |
| Uterus | 1.35 | 0.16 | 0.91 | 0.25 | 0.74 | 0.17 |
| Intestine | 1.81 | 0.58 | 1.47 | 0.60 | 1.38 | 0.32 |

TABLE 8

Tumor/tissue quotient of [$^{14}$C]5-glutamic acid in the murine, syngeneic, B16 melanoma in C57Bl6 mice after single intravenous administration.

| Tu/Ti qu. | | | |
|---|---|---|---|
| Spleen | 0.65 | 0.88 | 1.37 |
| Liver | 0.53 | 0.79 | 0.80 |
| Kidney | 0.42 | 1.03 | 1.07 |
| Lung | 0.33 | 1.18 | 1.18 |
| Heart | 0.41 | 1.11 | 1.88 |
| Brain | 5.59 | 7.66 | 10.59 |
| Fat | 1.80 | 5.36 | 6.64 |
| Muscle | 1.08 | 2.44 | 3.53 |
| Skin | 1.44 | 3.23 | 3.47 |
| Blood | 2.19 | 2.56 | 2.64 |
| Stomach | 0.46 | 0.49 | 0.61 |
| Intestine | 0.68 | 0.70 | 0.71 |
| Ovary | 0.47 | 1.01 | 0.83 |
| Uterus | 0.91 | 1.13 | 1.33 |

The invention claimed is:

1. A compound of the formula:

e)

f)

g)

h)

i)

j)

k)

l)

2. A process for the preparation of compounds of claim 1, comprising
reacting a precursor compound of the formula (II)

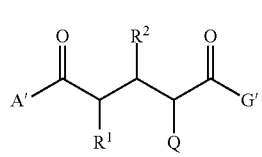
(II)

Wherein
A' represents hydroxyl, or $NH_2$,
G' represents hydroxyl,
$R^2$ represents hydrogen,
$R^1$ represents unbranched E-$C_1$ or E-$C_3$ alkyl, or unbranched E-$C_2$-$C_3$ alkoxy,
E represents
a) chloro,
b) bromo,
c) mesyloxy,
d) trifluoromesyloxy,
e) nonafluorobutyloxy, or
f) tosyloxy,
Q represents
a) N(H)-tert-butoxycarbonyl,
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
g) N(H)-2,2,2-trichloroethoxycarbonyl,
h) N(H)-1,1-dimethylpropynyl,
i) N(H)-1-methyl-1-phenylethoxycarbonyl,
j) N(H)-1-methyl-1-(4-biphenylyl)ethoxycarbonyl,
k) N(H)-cyclobutylcarbonyl,
l) N(H)-1-methylcyclobutylcarbonyl,
m) N(H)-vinylcarbonyl,
n) N(H)-allylcarbonyl,
o) N(H)-adamantylcarbonyl,
p) N(H)-diphenylmethylcarbonyl,
q) N(H)-cinnamylcarbonyl,
r) N(H)-formyl,
s) N(H)-benzoyl,
t) N(H)-trityl,
u) N(H)-p-methoxyphenyldiphenylmethyl,
v) N(H)-di(p-methoxyphenyl)phenylmethyl,
w)

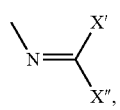

or
x) N-(tert-butoxycarbonyl)$_2$,
X' and X" independently of one another represent
a) branched or unbranched $C_1$-$C_5$ alkyl,
b) substituted or unsubstituted aryl or
c) aralkyl,
or diastereomers or enantiomers thereof,
with a F-18 fluoride.

3. A method for the diagnosis of tumors, comprising imaging a patient to whom a compound according to claim 1 has been administered.

4. A compound as claimed in claim 1, that is suitable for PET diagnostics in a dose range of 37-600 MBq.

5. A compound as claimed in claim 4, that is suitable in a dose range of 150 MBq-370 MBq.

6. The compound according to claim 1, of the formula:

g)
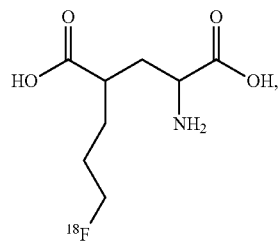

h)
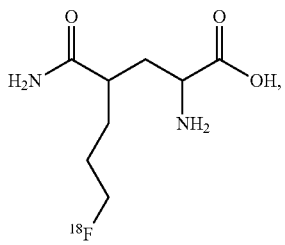

k)
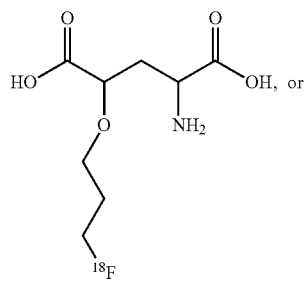

l)
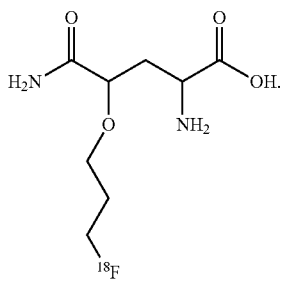

7. The compound according to claim 1, of the formula:

g)
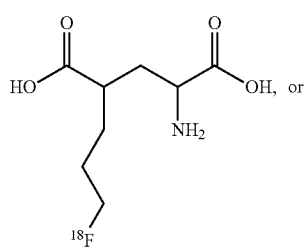

-continued
h)
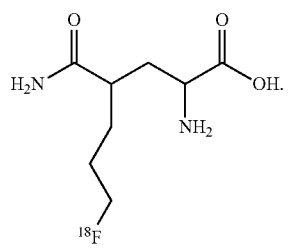
8. The compound according to claim 1, of the formula:
g)
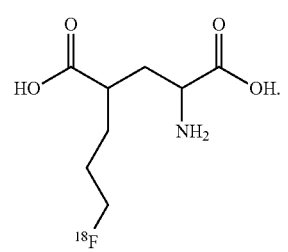
* * * * *